(12) United States Patent
Wahr et al.

(10) Patent No.: US 9,078,630 B2
(45) Date of Patent: *Jul. 14, 2015

(54) CLOSURE DEVICES, RELATED DELIVERY METHODS AND TOOLS, AND RELATED METHODS OF USE

(75) Inventors: Dennis W. Wahr, Ann Arbor, MI (US);
David J. Blaeser, Champlin, MN (US);
Peter T. Keith, St. Paul, MN (US);
Thomas V. Ressemann, St. Cloud, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 459 days.

This patent is subject to a terminal disclaimer.

(21) Appl. No.: 12/781,573

(22) Filed: May 17, 2010

(65) Prior Publication Data
US 2010/0234882 A1    Sep. 16, 2010

Related U.S. Application Data

(60) Continuation of application No. 11/198,325, filed on Aug. 8, 2005, now Pat. No. 7,717,937, which is a division of application No. 09/870,813, filed on Jun. 1, 2001, now Pat. No. 7,338,514.

(51) Int. Cl.
| A61B 17/00 | (2006.01) |
| A61B 18/14 | (2006.01) |
| A61B 18/00 | (2006.01) |

(52) U.S. Cl.
CPC .......... *A61B 17/0057* (2013.01); *A61B 18/1492* (2013.01); *A61B 2017/00243* (2013.01);
(Continued)

(58) Field of Classification Search
CPC .................. A61B 17/0057; A61B 2017/00243;
A61B 2017/00592; A61B 2017/00606; A61B 2017/00623; A61B 2018/00273; A61B 17/12109; A61B 17/1214; A61B 17/1215; A61B 17/12177; A61B 17/12172; A61B 17/12181; A61B 2017/00575; A61B 2017/00597; A61B 17/00
USPC ......... 606/213, 215, 216, 217, 218, 219, 151, 606/153, 157, 139, 232; 227/1, 175.1, 227/179.1, 181.1, 26, 28, 29, 30, 31, 19
See application file for complete search history.

(56) References Cited

U.S. PATENT DOCUMENTS

| 3,221,746 A | 12/1965 | Noble |
| 3,402,710 A | 9/1968 | Paleschuck |

(Continued)

FOREIGN PATENT DOCUMENTS

| AU | 79531 | 3/1975 |
| AU | 670239 A | 1/1994 |

(Continued)

OTHER PUBLICATIONS

UU. Babic, MD, "Experience with ASDOS for Transcatheter Closure of Atrial Septal Defect and Patent Foramen Ovale," Current InterventionalCardiology Reports 2:177-183 (2000).

(Continued)

*Primary Examiner* — Katherine Dowe
*Assistant Examiner* — Sidharth Kapoor
(74) *Attorney, Agent, or Firm* — Lerner, David, Littenberg, Krumholz & Mentlik, LLP

(57) ABSTRACT

A device for sealing a patent foramen ovale (PFO) in the heart is provided. The device includes a left atrial anchor adapted to be placed in a left atrium of the heart, a right atrial anchor adapted to be placed in a right atrium of the heart, and an elongate member adapted to extend through the passageway and connect the left and right atrial anchors. The right atrial anchor preferably includes a plurality of arms and a cover attached to the arms. The left atrial anchor also includes a plurality of arms and preferably does not include a cover. Preferably, the elongate member has a first end of fixedly connected to the left atrial anchor and a portion, proximal to the first end, releasably connected to the right atrial anchor. Preferably, the elongate member is flexible.

32 Claims, 24 Drawing Sheets

(52) U.S. Cl.
CPC ............... *A61B2017/00575* (2013.01); *A61B 2017/00592* (2013.01); *A61B 2017/00597* (2013.01); *A61B 2017/00606* (2013.01); *A61B 2017/00619* (2013.01); *A61B 2017/00623* (2013.01); *A61B 2018/00214* (2013.01); *A61B 2018/00273* (2013.01); *A61B 2018/00351* (2013.01)

(56) References Cited

U.S. PATENT DOCUMENTS

| | | | |
|---|---|---|---|
| 3,540,431 A | 11/1970 | Mobin-Ubdin | |
| 3,620,212 A | 11/1971 | Fannon, Jr. et al. | |
| 3,638,388 A | 2/1972 | Crookston | |
| 3,638,652 A | 2/1972 | Kelley | |
| 3,657,744 A | 4/1972 | Ersek | |
| 3,844,302 A | 10/1974 | Klein | |
| 3,874,388 A * | 4/1975 | King et al. | 606/232 |
| 4,007,743 A * | 2/1977 | Blake | 606/232 |
| 4,041,090 A | 8/1977 | McClure | |
| 4,041,931 A | 8/1977 | Elliott et al. | |
| 4,083,162 A | 4/1978 | Regan et al. | |
| 4,214,587 A | 7/1980 | Sakura, Jr. | |
| 4,309,776 A | 1/1982 | Berguer | |
| 4,341,218 A | 7/1982 | U | |
| 4,368,736 A | 1/1983 | Kaster | |
| 4,485,816 A | 12/1984 | Krumme | |
| 4,503,569 A | 3/1985 | Dotter | |
| 4,592,754 A | 6/1986 | Gupte et al. | |
| 4,603,693 A | 8/1986 | Conta et al. | |
| 4,617,932 A | 10/1986 | Kornberg | |
| 4,619,246 A | 10/1986 | Molgaard-Nielsen et al. | |
| 4,629,451 A | 12/1986 | Winters et al. | |
| 4,649,922 A | 3/1987 | Wiktor | |
| 4,665,906 A | 5/1987 | Jervis | |
| 4,681,588 A | 7/1987 | Ketharanathan | |
| 4,710,192 A | 12/1987 | Liotta et al. | |
| 4,733,665 A | 3/1988 | Palmaz | |
| 4,739,762 A | 4/1988 | Palmaz | |
| 4,748,982 A | 6/1988 | Horzewski et al. | |
| 4,776,337 A | 10/1988 | Palmaz | |
| 4,787,899 A | 11/1988 | Lazarus | |
| 4,826,487 A | 5/1989 | Winter | |
| 4,832,055 A | 5/1989 | Palestrant | |
| 4,836,204 A | 6/1989 | Landymore et al. | |
| 4,917,089 A | 4/1990 | Sideris | |
| 4,921,484 A | 5/1990 | Hillstead | |
| 4,994,069 A | 2/1991 | Ritchart et al. | |
| 5,041,082 A | 8/1991 | Shiber | |
| 5,041,090 A | 8/1991 | Scheglov et al. | |
| 5,042,707 A | 8/1991 | Taheri | |
| 5,052,386 A | 10/1991 | Fischer, Jr. | |
| 5,064,435 A | 11/1991 | Porter | |
| 5,067,489 A | 11/1991 | Lind | |
| 5,067,957 A | 11/1991 | Jervis | |
| 5,078,736 A | 1/1992 | Behl | |
| 5,098,440 A | 3/1992 | Hillstead | |
| 5,104,399 A | 4/1992 | Lazarus | |
| 5,108,420 A | 4/1992 | Marks | |
| 5,122,136 A | 6/1992 | Guglielmi et al. | |
| 5,122,156 A | 6/1992 | Granger et al. | |
| 5,135,467 A | 8/1992 | Citron | |
| 5,147,370 A | 9/1992 | McNamara et al. | |
| 5,171,233 A | 12/1992 | Amplatz et al. | |
| 5,171,259 A | 12/1992 | Inoue | |
| 5,176,692 A | 1/1993 | Wilk et al. | |
| 5,190,536 A | 3/1993 | Wood et al. | |
| 5,192,301 A * | 3/1993 | Kamiya et al. | 606/213 |
| 5,207,695 A | 5/1993 | Trout, III | |
| 5,211,658 A | 5/1993 | Clouse | |
| 5,211,683 A | 5/1993 | Maginot | |
| 5,234,447 A | 8/1993 | Kaster et al. | |
| 5,234,458 A | 8/1993 | Metais | |
| 5,246,445 A | 9/1993 | Yachia et al. | |
| 5,254,133 A | 10/1993 | Seid | |
| 5,258,000 A | 11/1993 | Gianturco | |
| 5,258,042 A | 11/1993 | Mehta | |
| 5,269,809 A * | 12/1993 | Hayhurst et al. | 606/232 |
| 5,275,622 A | 1/1994 | Lazarus et al. | |
| 5,284,486 A | 2/1994 | Kotula et al. | |
| 5,284,488 A | 2/1994 | Sideris | |
| 5,304,184 A | 4/1994 | Hathaway et al. | |
| 5,304,220 A | 4/1994 | Maginot | |
| 5,306,234 A | 4/1994 | Johnson | |
| 5,316,023 A | 5/1994 | Palmaz et al. | |
| 5,334,217 A | 8/1994 | Das | |
| 5,342,393 A | 8/1994 | Stack | |
| 5,350,398 A | 9/1994 | Pavcnik et al. | |
| 5,350,399 A | 9/1994 | Erlebacher et al. | |
| 5,354,309 A | 10/1994 | Schnepp-Pesch et al. | |
| 5,354,336 A | 10/1994 | Kelman et al. | |
| 5,360,443 A | 11/1994 | Barone et al. | |
| 5,366,462 A | 11/1994 | Kaster et al. | |
| 5,375,612 A | 12/1994 | Cottenceau et al. | |
| 5,385,562 A | 1/1995 | Adams et al. | |
| 5,387,235 A | 2/1995 | Chuter | |
| 5,391,156 A | 2/1995 | Hildwein et al. | |
| 5,397,345 A | 3/1995 | Lazarus | |
| 5,397,355 A | 3/1995 | Marin et al. | |
| 5,417,699 A | 5/1995 | Klein et al. | |
| 5,425,744 A | 6/1995 | Fagan et al. | |
| 5,433,497 A | 7/1995 | Koenig | |
| 5,433,727 A | 7/1995 | Sideris | |
| 5,443,454 A | 8/1995 | Tanabe et al. | |
| 5,443,478 A | 8/1995 | Purdy | |
| 5,443,497 A | 8/1995 | Venbrux | |
| 5,451,235 A | 9/1995 | Lock et al. | |
| 5,452,733 A | 9/1995 | Sterman et al. | |
| 5,456,693 A | 10/1995 | Conston et al. | |
| 5,456,712 A | 10/1995 | Maginot | |
| 5,464,408 A | 11/1995 | Duc | |
| 5,466,242 A | 11/1995 | Mori | |
| 5,478,354 A | 12/1995 | Tovey et al. | |
| 5,486,193 A | 1/1996 | Bourne et al. | |
| 5,489,295 A | 2/1996 | Piplani et al. | |
| 5,490,856 A | 2/1996 | Person et al. | |
| 5,496,365 A | 3/1996 | Sgro | |
| 5,507,769 A | 4/1996 | Marin et al. | |
| 5,522,790 A | 6/1996 | Moll et al. | |
| 5,522,822 A | 6/1996 | Phelps et al. | |
| 5,522,836 A | 6/1996 | Palermo | |
| 5,522,880 A | 6/1996 | Barone et al. | |
| 5,522,882 A | 6/1996 | Gaterud et al. | |
| 5,527,292 A | 6/1996 | Adams et al. | |
| 5,527,322 A | 6/1996 | Klein et al. | |
| 5,527,338 A | 6/1996 | Purdy | |
| 5,531,699 A * | 7/1996 | Tomba et al. | 604/170.02 |
| 5,545,214 A | 8/1996 | Stevens | |
| 5,549,619 A * | 8/1996 | Peters et al. | 606/151 |
| 5,562,728 A | 10/1996 | Lazarus et al. | |
| 5,593,422 A * | 1/1997 | Muijs Van de Moer et al. | 606/213 |
| 5,597,378 A | 1/1997 | Jervis | |
| 5,607,444 A | 3/1997 | Lam | |
| 5,614,204 A | 3/1997 | Cochrum | |
| 5,617,878 A | 4/1997 | Taheri | |
| 5,618,311 A | 4/1997 | Gryskiewicz | |
| 5,634,292 A | 6/1997 | Kitterman | |
| 5,634,936 A | 6/1997 | Linden et al. | |
| 5,645,558 A | 7/1997 | Horton | |
| 5,653,747 A | 8/1997 | Dereume | |
| 5,669,933 A | 9/1997 | Simon et al. | |
| 5,676,670 A | 10/1997 | Kim | |
| 5,681,336 A | 10/1997 | Clement et al. | |
| 5,693,067 A | 12/1997 | Purdy | |
| 5,693,083 A | 12/1997 | Baker et al. | |
| 5,695,504 A | 12/1997 | Gifford, III et al. | |
| 5,702,412 A | 12/1997 | Popov et al. | |
| 5,702,421 A * | 12/1997 | Schneidt | 606/213 |
| 5,709,224 A | 1/1998 | Behl et al. | |
| 5,709,707 A | 1/1998 | Lock et al. | |
| 5,725,552 A | 3/1998 | Kotula et al. | |
| 5,725,568 A | 3/1998 | Hastings | |
| 5,733,294 A | 3/1998 | Forber et al. | |

(56) References Cited

U.S. PATENT DOCUMENTS

| | | | |
|---|---|---|---|
| 5,735,290 A | 4/1998 | Sterman et al. |
| 5,735,893 A | 4/1998 | Lau et al. |
| 5,741,297 A | 4/1998 | Simon |
| 5,749,894 A | 5/1998 | Engelson |
| 5,755,778 A | 5/1998 | Kleshinski |
| 5,766,219 A | 6/1998 | Horton |
| 5,775,778 A | 7/1998 | Riley et al. |
| 5,776,097 A | 7/1998 | Massoud |
| 5,776,162 A | 7/1998 | Kleshinski |
| 5,782,860 A | 7/1998 | Epstein et al. |
| 5,797,960 A | 8/1998 | Stevens et al. |
| 5,830,228 A | 11/1998 | Knapp et al. |
| 5,833,698 A | 11/1998 | Hinchliffe et al. |
| 5,836,968 A | 11/1998 | Simon et al. |
| 5,840,064 A | 11/1998 | Liprie |
| 5,843,118 A | 12/1998 | Sepetka et al. |
| 5,843,164 A | 12/1998 | Frantzen et al. |
| 5,843,170 A | 12/1998 | Ahn |
| 5,843,175 A | 12/1998 | Frantzen |
| 5,843,176 A | 12/1998 | Weier |
| 5,846,261 A | 12/1998 | Kotula et al. |
| 5,849,005 A | 12/1998 | Garrison et al. |
| 5,853,419 A | 12/1998 | Imran |
| 5,853,422 A | 12/1998 | Huebsch et al. |
| 5,861,003 A | 1/1999 | Latson et al. |
| 5,865,791 A | 2/1999 | Whayne et al. |
| 5,868,762 A | 2/1999 | Cragg et al. |
| 5,879,366 A | 3/1999 | Shaw et al. |
| 5,885,258 A | 3/1999 | Sachdeva et al. |
| 5,891,558 A | 4/1999 | Bell et al. |
| 5,904,680 A | 5/1999 | Kordis et al. |
| 5,904,703 A | 5/1999 | Gilson |
| 5,906,207 A | 5/1999 | Shen |
| 5,910,155 A | 6/1999 | Ratcliff et al. |
| 5,919,200 A | 7/1999 | Stambaugh et al. |
| 5,921,995 A | 7/1999 | Kleshinski |
| 5,922,022 A | 7/1999 | Nash et al. |
| 5,935,148 A | 8/1999 | Villar et al. |
| 5,944,738 A | 8/1999 | Amplatz et al. |
| 5,976,159 A | 11/1999 | Bolduc et al. |
| 5,976,178 A | 11/1999 | Goldsteen et al. |
| 6,013,190 A | 1/2000 | Berg et al. |
| 6,021,340 A | 2/2000 | Randolph et al. |
| 6,024,756 A * | 2/2000 | Huebsch et al. ............ 606/213 |
| 6,026,814 A | 2/2000 | LaFontaine et al. |
| 6,035,856 A | 3/2000 | LaFontaine et al. |
| 6,036,702 A | 3/2000 | Bachinski et al. |
| 6,036,716 A | 3/2000 | Kruchinin et al. |
| 6,074,416 A | 6/2000 | Berg et al. |
| 6,076,012 A | 6/2000 | Swanson et al. |
| 6,079,414 A | 6/2000 | Roth |
| 6,080,182 A | 6/2000 | Shaw et al. |
| 6,113,612 A | 9/2000 | Swanson et al. |
| 6,120,432 A | 9/2000 | Sullivan et al. |
| 6,123,715 A | 9/2000 | Amplatz |
| 6,124,523 A | 9/2000 | Banas et al. |
| 6,132,438 A | 10/2000 | Fleischman et al. |
| 6,152,144 A | 11/2000 | Lesh et al. |
| 6,165,196 A | 12/2000 | Stack et al. |
| 6,168,622 B1 | 1/2001 | Mazzocchi |
| 6,171,329 B1 | 1/2001 | Shaw et al. |
| 6,174,322 B1 | 1/2001 | Schneidt |
| 6,193,734 B1 | 2/2001 | Bolduc et al. |
| 6,206,907 B1 | 3/2001 | Marino et al. |
| 6,210,338 B1 | 4/2001 | Afremov et al. |
| 6,214,029 B1 | 4/2001 | Thill et al. |
| 6,231,561 B1 | 5/2001 | Frazier et al. |
| 6,241,678 B1 | 6/2001 | Afremov et al. |
| 6,245,012 B1 | 6/2001 | Kleshinski |
| 6,290,674 B1 | 9/2001 | Roue et al. |
| 6,325,815 B1 | 12/2001 | Kusleika et al. |
| 6,332,863 B1 | 12/2001 | Schweich, Jr. et al. |
| 6,334,864 B1 | 1/2002 | Amplatz et al. |
| 6,355,052 B1 | 3/2002 | Neuss et al. |
| 6,368,338 B1 | 4/2002 | Konya et al. |
| 6,368,339 B1 | 4/2002 | Amplatz |
| 6,371,971 B1 | 4/2002 | Tsugita et al. |
| 6,379,368 B1 | 4/2002 | Corcoran et al. |
| 6,391,044 B1 | 5/2002 | Yadav et al. |
| 6,402,746 B1 | 6/2002 | Whayne et al. |
| 6,402,772 B1 | 6/2002 | Amplatz et al. |
| 6,419,669 B1 | 7/2002 | Frazier et al. |
| 6,432,123 B2 | 8/2002 | Schwartz et al. |
| 6,436,088 B2 | 8/2002 | Frazier et al. |
| 6,440,152 B1 | 8/2002 | Gainor et al. |
| 6,447,531 B1 | 9/2002 | Amplatz |
| 6,458,100 B2 | 10/2002 | Roue et al. |
| 6,468,291 B2 | 10/2002 | Bates et al. |
| 6,468,301 B1 | 10/2002 | Amplatz et al. |
| D466,936 S | 12/2002 | Shaw et al. |
| 6,491,707 B2 | 12/2002 | Makower et al. |
| 6,506,204 B2 | 1/2003 | Mazzocchi |
| 6,508,828 B1 * | 1/2003 | Akerfeldt et al. ............ 606/215 |
| 6,511,496 B1 | 1/2003 | Huter et al. |
| 6,517,551 B1 | 2/2003 | Driskill |
| 6,527,746 B1 | 3/2003 | Oslund et al. |
| 6,537,299 B1 | 3/2003 | Hogendijk et al. |
| 6,540,712 B1 | 4/2003 | Parodi et al. |
| 6,551,303 B1 | 4/2003 | Van Tassel et al. |
| 6,551,344 B2 | 4/2003 | Thill |
| 6,562,058 B2 | 5/2003 | Seguin et al. |
| 6,599,308 B2 | 7/2003 | Amplatz |
| 6,616,675 B1 | 9/2003 | Evard et al. |
| 6,623,508 B2 | 9/2003 | Shaw et al. |
| 6,641,557 B1 | 11/2003 | Frazier et al. |
| 6,650,923 B1 | 11/2003 | Lesh et al. |
| 6,652,555 B1 | 11/2003 | VanTassel et al. |
| 6,652,556 B1 * | 11/2003 | VanTassel et al. ............ 606/200 |
| 6,656,206 B2 | 12/2003 | Corcoran et al. |
| 6,660,015 B1 | 12/2003 | Berg et al. |
| 6,682,546 B2 | 1/2004 | Amplatz |
| 6,689,150 B1 | 2/2004 | VanTassel et al. |
| 6,712,804 B2 | 3/2004 | Roue et al. |
| 6,712,836 B1 | 3/2004 | Berg et al. |
| 6,776,784 B2 | 8/2004 | Ginn |
| 6,790,218 B2 * | 9/2004 | Jayaraman ............ 606/191 |
| 6,860,895 B1 | 3/2005 | Akerfeldt et al. |
| 6,911,037 B2 | 6/2005 | Gainor et al. |
| 6,913,614 B2 | 7/2005 | Marino et al. |
| 7,128,073 B1 * | 10/2006 | van der Burg et al. ........ 128/887 |
| 7,338,514 B2 | 3/2008 | Wahr et al. |
| 2001/0000797 A1 | 5/2001 | Mazzocchi |
| 2001/0014800 A1 | 8/2001 | Frazier et al. |
| 2001/0021872 A1 | 9/2001 | Bailey et al. |
| 2001/0034537 A1 | 10/2001 | Shaw et al. |
| 2001/0037129 A1 | 11/2001 | Thill |
| 2001/0041914 A1 | 11/2001 | Frazier et al. |
| 2002/0010481 A1 * | 1/2002 | Jayaraman ............ 606/151 |
| 2002/0022860 A1 | 2/2002 | Borillo et al. |
| 2002/0026094 A1 | 2/2002 | Roth |
| 2002/0029061 A1 | 3/2002 | Amplatz et al. |
| 2002/0035374 A1 | 3/2002 | Borillo et al. |
| 2002/0042625 A1 | 4/2002 | Stack et al. |
| 2002/0068950 A1 | 6/2002 | Corcoran et al. |
| 2002/0111647 A1 | 8/2002 | Khairkhahan et al. |
| 2002/0123759 A1 | 9/2002 | Amplatz |
| 2002/0123760 A1 | 9/2002 | Amplatz |
| 2002/0138094 A1 | 9/2002 | Borillo et al. |
| 2002/0138095 A1 | 9/2002 | Mazzocchi et al. |
| 2002/0161395 A1 | 10/2002 | Douk et al. |
| 2002/0169474 A1 | 11/2002 | Kusleika et al. |
| 2002/0169475 A1 | 11/2002 | Gainor et al. |
| 2002/0183787 A1 | 12/2002 | Wahr et al. |
| 2002/0198561 A1 | 12/2002 | Amplatz |
| 2002/0198563 A1 | 12/2002 | Gainor et al. |
| 2003/0023262 A1 | 1/2003 | Welch |
| 2003/0023266 A1 | 1/2003 | Borillo et al. |
| 2003/0028213 A1 | 2/2003 | Thill et al. |
| 2003/0045901 A1 | 3/2003 | Opolski |
| 2003/0057156 A1 | 3/2003 | Peterson et al. |
| 2003/0120337 A1 | 6/2003 | Van Tassel et al. |
| 2003/0139819 A1 | 7/2003 | Beer et al. |
| 2003/0144694 A1 | 7/2003 | Chanduszko et al. |
| 2003/0181942 A1 | 9/2003 | Sutton et al. |

(56) References Cited

U.S. PATENT DOCUMENTS

| | | |
|---|---|---|
| 2003/0191495 A1 | 10/2003 | Ryan et al. |
| 2003/0191526 A1 | 10/2003 | Van Tassel et al. |
| 2003/0195530 A1 | 10/2003 | Thill |
| 2003/0195555 A1 | 10/2003 | Khairkhahan et al. |
| 2003/0199923 A1 | 10/2003 | Khairkhahan et al. |
| 2003/0204203 A1 | 10/2003 | Khairkhahan et al. |
| 2003/0212432 A1 | 11/2003 | Khairkhahan et al. |
| 2003/0225421 A1 | 12/2003 | Peavey et al. |
| 2004/0073242 A1 | 4/2004 | Chanduszko |
| 2004/0092973 A1 | 5/2004 | Chanduszko et al. |
| 2004/0098047 A1 | 5/2004 | Frazier et al. |
| 2004/0098121 A1 | 5/2004 | Opolski |
| 2004/0133236 A1 | 7/2004 | Chanduszko |
| 2004/0143277 A1 | 7/2004 | Marino et al. |
| 2004/0143291 A1 | 7/2004 | Corcoran et al. |
| 2004/0143293 A1 | 7/2004 | Marino et al. |
| 2004/0143294 A1 | 7/2004 | Corcoran et al. |
| 2004/0162569 A1 | 8/2004 | Sikora et al. |
| 2004/0176799 A1 | 9/2004 | Chanduszko et al. |
| 2004/0186486 A1 | 9/2004 | Roue et al. |
| 2004/0193147 A1 | 9/2004 | Malecki et al. |
| 2004/0215230 A1 | 10/2004 | Frazier et al. |
| 2004/0225324 A1 | 11/2004 | Marino et al. |
| 2004/0230185 A1 | 11/2004 | Malecki et al. |
| 2004/0267191 A1 | 12/2004 | Gifford et al. |
| 2005/0021016 A1 | 1/2005 | Malecki et al. |
| 2005/0033327 A1 | 2/2005 | Gainor et al. |
| 2005/0034735 A1 | 2/2005 | Deem et al. |
| 2005/0038470 A1 | 2/2005 | van der Burg et al. |
| 2005/0043711 A1 | 2/2005 | Corcoran et al. |
| 2005/0043759 A1 | 2/2005 | Chanduszko |
| 2005/0059983 A1 | 3/2005 | Opolski et al. |
| 2005/0065546 A1 | 3/2005 | Corcoran et al. |
| 2005/0065547 A1 | 3/2005 | Marino et al. |
| 2005/0065548 A1 | 3/2005 | Marino et al. |
| 2005/0080406 A1 | 4/2005 | Malecki et al. |
| 2005/0090857 A1 | 4/2005 | Kusleika et al. |
| 2005/0101984 A1 | 5/2005 | Chanduszko et al. |
| 2005/0113861 A1 | 5/2005 | Corcoran et al. |
| 2005/0113868 A1 | 5/2005 | Devellian et al. |
| 2005/0119675 A1 | 6/2005 | Adams et al. |
| 2005/0131401 A1 | 6/2005 | Malecki et al. |
| 2005/0131460 A1 | 6/2005 | Gifford et al. |
| 2005/0155612 A1 | 7/2005 | Matsuura et al. |
| 2007/0066994 A1 | 3/2007 | Blaeser et al. |

FOREIGN PATENT DOCUMENTS

| | | |
|---|---|---|
| CA | 2057018 | 10/1991 |
| DE | 233303 | 9/1909 |
| DE | 2822603 | 11/1979 |
| DE | 19542733 | 7/1997 |
| DE | 29713335 | 10/1997 |
| EP | 0362113 | 4/1990 |
| EP | 0539237 | 4/1993 |
| EP | 0541063 | 5/1993 |
| EP | 0637454 | 2/1995 |
| EP | 0680734 | 11/1995 |
| EP | 0684022 | 11/1995 |
| EP | 0701800 | 3/1996 |
| EP | 0712614 | 5/1996 |
| EP | 0732088 | 9/1996 |
| EP | 0732089 | 9/1996 |
| EP | 0807444 | 11/1997 |
| EP | 1013227 | 6/2000 |
| EP | 1175867 | 1/2002 |
| EP | 1281355 | 2/2003 |
| FR | 2641692 | 7/1990 |
| GB | 489316 | 7/1938 |
| GB | 2269321 | 2/1994 |
| WO | 8908433 | 9/1989 |
| WO | 9105088 A1 | 4/1991 |
| WO | 9300868 | 1/1993 |
| WO | 9313712 | 7/1993 |
| WO | 9320757 | 10/1993 |
| WO | 9401056 | 1/1994 |
| WO | 9521592 | 8/1995 |
| WO | 9526695 | 10/1995 |
| WO | 9528885 | 11/1995 |
| WO | 9532757 | 12/1995 |
| WO | 9601591 | 1/1996 |
| WO | 9601599 | 1/1996 |
| WO | 9614808 | 5/1996 |
| WO | 9618361 | 6/1996 |
| WO | 9622745 | 8/1996 |
| WO | 9625897 | 8/1996 |
| WO | 9640356 | 12/1996 |
| WO | 9713463 | 4/1997 |
| WO | 9713471 | 4/1997 |
| WO | 9727898 | 8/1997 |
| WO | 9741779 | 11/1997 |
| WO | 9742878 | 11/1997 |
| WO | 9801086 | 1/1998 |
| WO | 9802099 | 1/1998 |
| WO | 9803118 A1 | 1/1998 |
| WO | 9807399 | 2/1998 |
| WO | 9808462 | 3/1998 |
| WO | 9809671 | 3/1998 |
| WO | 9816161 | 4/1998 |
| WO | 9819629 | 5/1998 |
| WO | 9819631 | 5/1998 |
| WO | 9826732 | 6/1998 |
| WO | 9827868 | 7/1998 |
| WO | 9827894 | 7/1998 |
| WO | 9838939 | 9/1998 |
| WO | 9838941 A1 | 9/1998 |
| WO | 9838942 | 9/1998 |
| WO | 9842262 | 10/1998 |
| WO | 9855027 | 12/1998 |
| WO | 9907289 | 2/1999 |
| WO | 9917816 | 4/1999 |
| WO | 9938454 | 8/1999 |
| WO | 9939646 | 8/1999 |
| WO | 9962408 | 12/1999 |
| WO | 0010452 | 3/2000 |
| WO | 0012012 | 3/2000 |
| WO | 0016705 | 3/2000 |
| WO | 0027292 | 5/2000 |
| WO | 0056245 | 9/2000 |
| WO | 0115629 | 3/2001 |
| WO | 0117435 | 3/2001 |
| WO | 0130266 | 5/2001 |
| WO | 0130267 | 5/2001 |
| WO | 0130268 | 5/2001 |
| WO | 0172367 | 10/2001 |
| WO | 0187163 | 11/2001 |
| WO | 0191844 | 12/2001 |
| WO | 0215793 | 2/2002 |
| WO | 0224106 | 3/2002 |
| WO | 02098298 | 12/2002 |
| WO | 03009880 | 2/2003 |
| WO | 03053493 | 7/2003 |
| WO | 03059152 | 7/2003 |
| WO | 03082076 | 10/2003 |
| WO | 03103476 | 12/2003 |
| WO | 2005006990 | 1/2005 |
| WO | 2005027752 | 3/2005 |
| WO | 2005039419 | 5/2005 |

OTHER PUBLICATIONS

Brochure and instructions for use for "CardioSeal.RTM. Septal Occlusion System," An Alternative FDA approved! Solution for Patients Needing Closure of Ventricular Septal Defects, NMT Medical, Inc., 1999, pp. 1-24.

European Search Report for EP 05010346 (dated Jun. 22, 2005).

Terry King et al., 'Secundum Atrial Septal Defect,' JAMA, vol. 235, No. 23, pp. 2506-2509, Jun. 1976.

Makram R, Ebeid, MD, "Percutaneous Catheter Closure of Secundum Atrial Septal Defects: A Review," J, Invas. Cardiol, 2002; 14: 25-31.

(56) References Cited

OTHER PUBLICATIONS

U.U. Babic, MD, 'Experience with ASDOS for Transcatheter Closure of Atrial Septal Defect and Patent Foramen Ovale,' Current Interventional Cardiology Reports, 2:177-183, (2000).
Brochure and instructions for Use for "CardioSeal® Septal Occlusion System," An Alternative FDA Approved Solution for Patients Needing Closure of Ventricular Septal Defects, NMT Medical Inc., 1999, pp. 1-24.
PCT Search Report of PCT/US03/13970.
U.S. Appl. No. 10/934,735, filed Sep. 7, 2004.
U.S. Appl. No. 11/522,157, filed Sep. 15, 2006.
U.S. Appl. No. 11/522,158, filed Sep. 15, 2006.
U.S. Appl. No. 11/522,193, filed Sep. 15, 2006.
U.S. Appl. No. 12/626,175, filed Nov. 25, 2009.
U.S. Appl. No. 10/411,152, filed Apr. 11, 2003.
U.S. Appl. No. 09/870,813, filed Jun. 1, 2001.
U.S. Appl. No. 11/185,951, filed Jul. 21, 2005.
U.S. Appl. No. 11/198,325, filed Aug. 8, 2005.

\* cited by examiner

CLOSURE DEVICES, RELATED DELIVERY METHODS AND TOOLS, AND RELATED METHODS OF USE

CROSS-REFERENCE TO RELATED APPLICATIONS

This application is a continuation of U.S. application Ser. No. 11/198,325, filed on Aug. 8, 2005, which is a divisional application of U.S. application Ser. No. 09/870,813, filed on Jun. 1, 2001, the disclosures of both of which are incorporated herein by reference.

FIELD OF THE INVENTION

This invention relates to devices for closing a passageway in a body, for example a patent foramen ovale in a heart, related methods and devices for delivering such closure devices, and related methods of using such closure devices for sealing the passageway.

BACKGROUND OF THE INVENTION

FIG. 20 shows a portion of a heart in longitudinal section, with the right atrium (RA), left atrium (LA), right ventricle (RV) and left ventricle (LV) shown. FIG. 20 also shows the septum primum (SP), a flap-like structure, which normally covers the foramen ovale, an opening in the septum secundum (SS) of the heart. In utero, the foramen ovals serves as a physiologic conduit for right-to-left shunting of blood in the fetal heart. After birth, with the establishment of pulmonary circulation, the increased left atrial blood flow and pressure presses the septum primum (SP) against the walls of the septum secundum (SS), covering the foramen ovale and resulting in functional closure of the foramen ovale. This closure is usually followed by anatomical closure of the foramen ovale due to fusion of the septum primum (SP) to the septum secundum (SS).

Where anatomical closure of the foramen ovale does not occur, a patent foramen ovale (PFO) is created. A patent foramen ovale is a persistent, usually flap-like opening between the atrial septum primum (SP) and septum secundum (SS) of a heart. A patent foramen ovals results when either partial or no fusion of the septum primum (SP) to the septum secundum (SS) occurs. In the case of partial fusion, a persistent passageway exists between the superior portion of the septum primum (SP) and septum secundum (SS). It is also possible that more than one passageway may exist between the septum primum (SP) and the septum secundum (SS).

Studies have shown that a relatively large percentage of adults have a patent foramen ovale (PFO). It is believed that embolism via a PFO may be a cause of a significant number of ischemic strokes, particularly in relatively young patients. It has been estimated that in 50% of cryptogenic strokes, a PFO is present. Patients suffering a cryptogenic stroke or a transient ischemic attack (TIA) in the presence of a PFO often are considered for medical therapy to reduce the risk of a recurrent embolic event.

Pharmacological therapy often includes oral anticoagulants or antiplatelet agents. These therapies may lead to certain side effects, including hemorrhaging. If pharmacologic therapy is unsuitable, open heart surgery may be employed to close a PFO with stitches, for example. Like other open surgical treatments, this surgery is highly invasive, risky, requires general anesthesia, and may result in lengthy recuperation.

Nonsurgical closure of PFOs is possible with umbrella-like devices developed for percutaneous closure of atrial septal defects (ASD) (a condition where there is not a septum primum (SP)). Many of these conventional devices used for ASDs, however, are technically complex, bulky, and difficult to deploy in a precise location. In addition, such devices may be difficult or impossible to retrieve and/or reposition should initial positioning not be satisfactory. Moreover, these devices are specially designed for ASDs and therefore may not be suitable to close and seal a PFO, particularly because the septum primum (SP) overlaps the septum secundum (SS).

SUMMARY OF THE INVENTION

In accordance with the invention, methods, tools, and devices for closing a passageway in a body, and more specifically closing a patent foramen ovale (PFO), are provided.

According to one aspect of the invention, a device for sealing a passageway in a human body is provided. The device comprises a first anchor adapted to be placed proximate a first end of the passageway, a second anchor adapted to be placed proximate a second end of the passageway, and an elongate member adapted to extend through the passageway and connect the first and second anchors, the elongate member having a first end fixedly connected to the first anchor and a second end that releasably connects to the second anchor.

According to another aspect of the invention, a device for sealing a passageway in a human body comprises a first anchor adapted to be placed proximate a first end of the passageway, a second anchor adapted to be placed proximate a second end of the passageway, and a flexible elongate member adapted to extend through the passageway and connect the first and second anchors, the elongate member capable of moving through the second anchor to vary a length of the elongate member between the first and second anchors.

According to another aspect of the invention, a device for sealing a passageway in a heart is provided. The device comprises a first anchor adapted to be placed proximate a first end of the passageway, a second anchor adapted to be placed proximate a second end of the passageway, and a flexible elongate member adapted to extend through the passageway and connect the first and second anchors, wherein the first anchor pivots relative to the elongate member and the second anchor pivots relative to the elongate member.

According to yet another aspect of the invention, a device for sealing a passageway in a heart comprises a first anchor adapted to be placed proximate a first end of the passageway, a second anchor adapted to be placed proximate a second end of the passageway, and a flexible elongate member adapted to extend through the passageway and connect the first and second anchors, wherein each of the first and second anchors is collapsible from a deployed state to a collapsed delivery state.

According to a further aspect of the invention, a device for sealing a patent foramen ovale in a heart is provided. The device includes a first anchor including a first plurality of arms adapted to be placed proximate a first end of the patent foramen ovate, a second anchor including a second plurality of arms adapted to be placed proximate a second end of the patent foramen ovate, and a flexible elongate member adapted to extend through the patent foramen ovale and connect the first and second anchors, the elongate member having a first end fixedly connected to the first anchor and a second end that releasably connects to the second anchor, and wherein each of the first and second plurality of arms are collapsible from a deployed state to a delivery state.

According to another aspect of the invention, an assembly for sealing a passageway in a heart is provided. The assembly comprises a positioning catheter capable of extending to the passageway, and a closure device capable of sealing the passageway, the closure device including a first anchor adapted to be placed proximate a first end of the passageway, a second anchor adapted to be placed proximate a second end of the passageway, and a flexible elongate member adapted to extend through the passageway and connect the first and second anchors, wherein the closure device is positionable within the positioning catheter in a first collapsed state and extendable from the positioning catheter in a second deployed state.

According to yet another aspect of the invention, an assembly for sealing a patent foramen ovale in a heart is provided. The assembly comprises a guide catheter capable of extending to the patent foramen ovale, a positioning catheter capable of extending through the guide catheter to a position near the patent foramen ovale, and a closure device capable of sealing the patent foramen ovale, the closure device including a first anchor having a first plurality of arms adapted to be placed proximate a first end of the patent foramen ovale, a second anchor having a second plurality of arms adapted to be placed proximate a second end of the patent foramen ovale, a flexible elongate member adapted to extend through the patent foramen ovale and connect the first and second anchors, and a releasable fixation mechanism that selectively engages a distal portion of the positioning catheter to releasably connect the second end of the elongate member to the second anchor, wherein the closure device is positionable within the positioning catheter in a first state wherein each of the first and second plurality of arms are collapsed and extendable from the positioning catheter in a second deployed state wherein each of the first and second plurality of arms are extended.

According to another aspect of the invention, a method of sealing a passageway in a heart is provided. The method comprises placing a first anchor proximate a first end of the passageway, placing a second anchor proximate a second end of the passageway, and moving the second anchor relative to the first anchor along a flexible elongate member disposed between the first and second anchors within the passageway.

According to another aspect of the invention, a method of placing a closure device to seal a passageway in a heart comprises advancing a catheter into a first end of the passageway and out a second end of the passageway, advancing a first anchor of a closure device out of a distal end of the catheter, withdrawing the catheter through the passageway, positioning the first anchor adjacent the second end of the passageway, advancing a second anchor of the closure device out of the distal end of the catheter, and positioning the second anchor of the closure device adjacent the first end of the passageway.

According to a further aspect of the invention, a method of delivering a closure device to a patent foramen ovale in a heart is provided. The method includes advancing a catheter into the right atrium of the heart, advancing the catheter through the patent foramen ovale into the left atrium of the heart, deploying a first anchor of the closure device in the left atrium, withdrawing the catheter into the right atrium of the heart, and deploying a second anchor of the closure device in the right atrium.

According to another aspect of the invention, a closure device for sealing a passageway in a heart comprises a left atrial anchor configured to close a first end of the passageway, a right atrial anchor configured to close a second end of the passageway, and a flexible elongate member connecting the left and right atrial anchors, wherein the elongate member has a first end fixedly connected to the left atrial anchor and wherein the right atrial anchor is movable with respect to the elongate member and is configured to releasably attach to the elongate member at any one of a plurality of points along a length of the elongate member.

According to another aspect of the invention, an assembly for sealing a passageway in a heart includes a guide catheter configured to extend from a point of entry into a body to the passageway, and a closure device capable of sealing the passageway, the closure device including a first anchor adapted to be placed proximate a first end of the passageway, a second anchor adapted to be placed proximate a second end of the passageway, and a flexible elongate member connecting the first and second anchors, wherein a first end of the elongate member is connected to the first anchor and wherein the elongate member extends through the second anchor and through the catheter to the point of entry into the body.

According to yet another aspect of the invention, a device for sealing a passageway in a human body comprises a first anchor adapted to be placed proximate a first end of the passageway, a second anchor adapted to be placed proximate a second end of the passageway, and a flexible elongate member adapted to extend through the passageway and connect the first and second anchors, the elongate member capable of moving through the second anchor to vary a tension of the elongate member.

According to another aspect of the invention, a device for closing a passageway in a human body comprises a first anchor adapted to be placed proximate a first end of the passageway, a second anchor adapted to be placed proximate a second end of the passageway, and a flexible elongate member adapted to extend through the passageway and connect the first and second anchors, the elongate member having a first end releasably connected to the first anchor and a second end releasably connected to the second anchor.

According to another aspect of the invention, a device for closing a passageway in a heart comprises a left atrial anchor adapted to be placed in a left atrium of the heart and including a plurality of uncovered arms, a right atrial anchor adapted to be placed in a right atrium of the heart and including a plurality of arms and a cover attached to the plurality of arms, and a flexible elongate member adapted to extend through the passageway and connect the left and right atrial anchors, the elongate member having a first end fixedly connected to the left atrial anchor and a second end releasably connected to the right atrial anchor.

According to another aspect of the invention, a device for sealing a passageway in a heart comprises a first anchor adapted to be placed proximate a first end of the passageway, the first anchor comprising a plurality of uncovered arms, a second anchor adapted to be placed proximate a second end of the passageway, the second anchor comprising a plurality of uncovered arms, and a flexible elongate member adapted to extend through the passageway and connect the first and second anchors, the elongate member having a first end fixedly connected to the first anchor and a second end that releasably connects to the second anchor.

Additional advantages of the invention will be set forth in part in the description which follows, and in part will be obvious from the description, or may be learned by practice of the invention. The objects and advantages of the invention will be realized and attained by means of the elements and combinations particularly pointed out in the appended claims.

The foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate several embodiments of the invention and together with the description, serve to explain the principles of the invention.

DESCRIPTION OF THE EMBODIMENTS

Reference will now be made in detail to embodiments of the invention, examples of which are illustrated in the accompanying drawings. Wherever possible, the same reference numbers will be used throughout the drawings to refer to the same or like parts.

The various Figures show embodiments of patent foramen ovale (PFO) closure devices, tools, devices and methods for delivery of the PFO closure devices, and methods of using the device to close a PFO. The devices and related methods are described herein in connection with use in sealing a PFO. These devices, however, also are suitable for closing other openings or passageways, including other such openings in the heart, for example atrial septal defects, ventricular septal defects, and patent ductus arterioses, and openings or passageways in other portions of a body such as an arteriovenous fistula. The invention therefore is not limited to use of the inventive closure devices to close PFOs.

Figure 1:
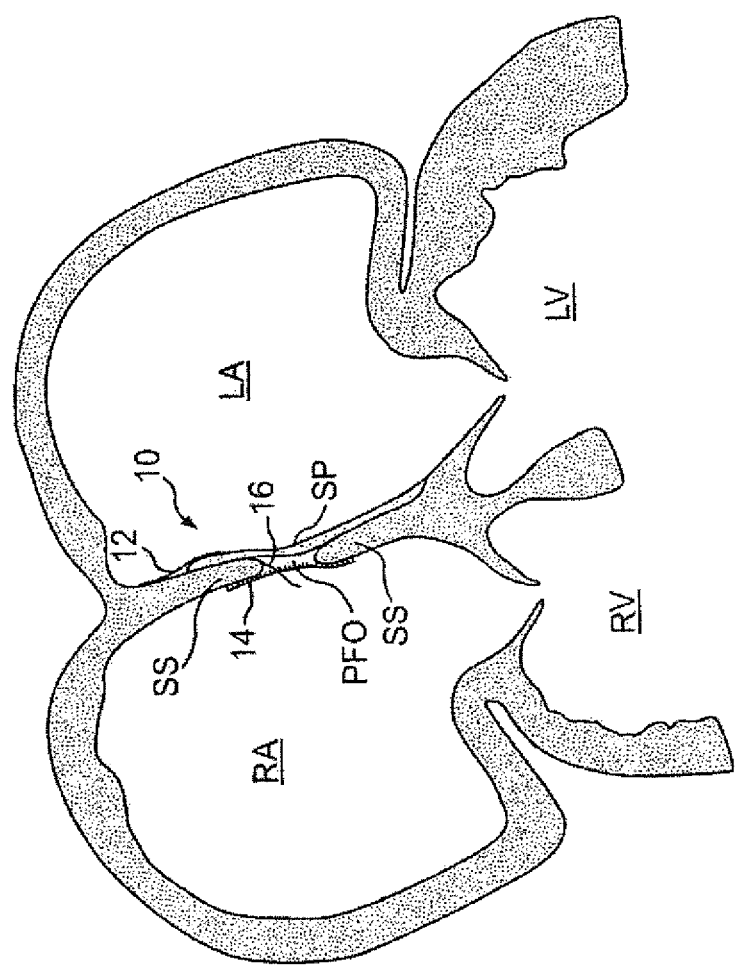
FIG. 1 is a closure device positioned in a heart to close a PFO, according to an embodiment of the present invention.
Figure 11:
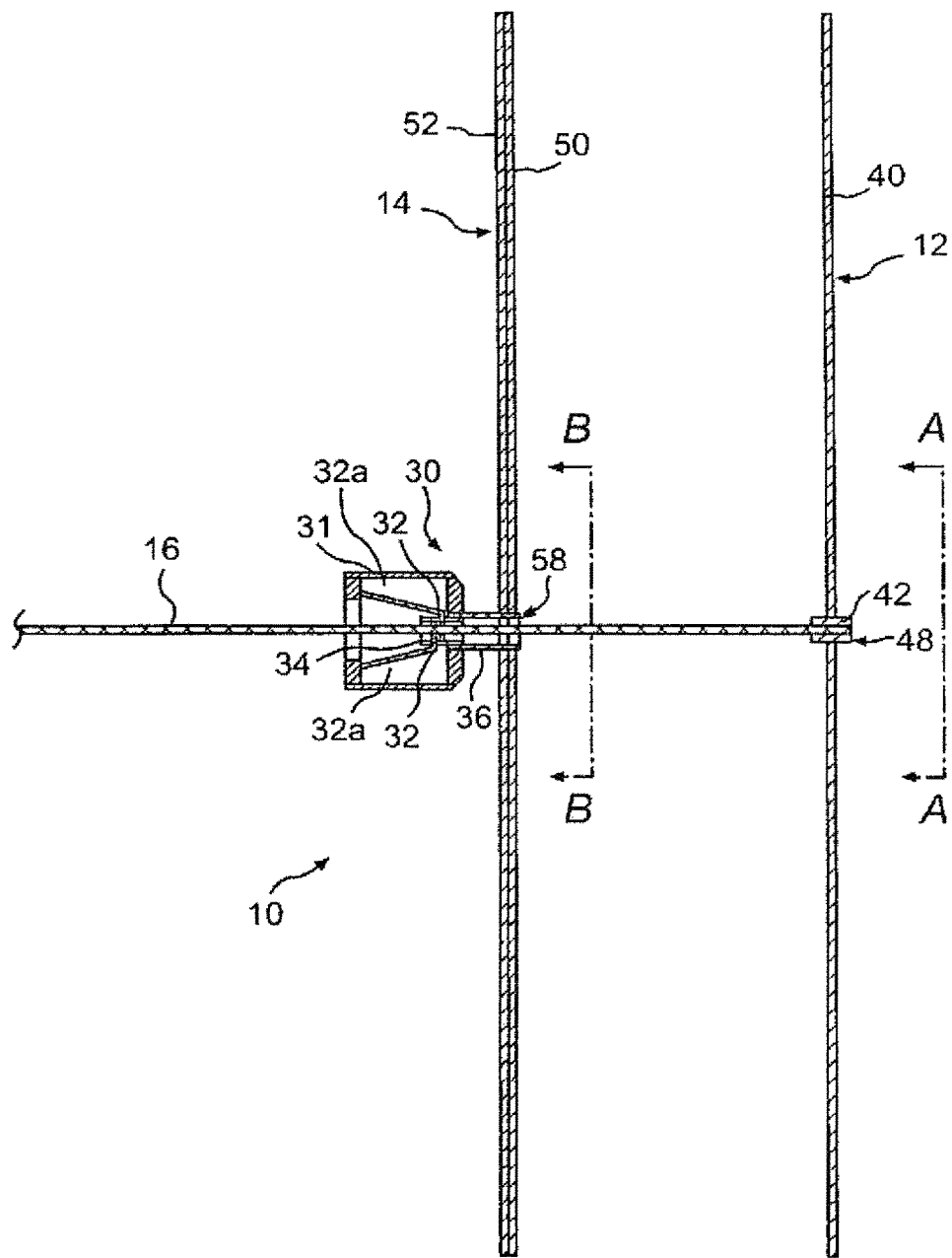
FIG. 11 is a cross-sectional side view of a closure device, including a sectional view of a fixation mechanism, according to an embodiment of the present invention.

FIGS. 1 and 11 show a PFO closure device 10 according to an embodiment of the present invention. In FIG. 1, device 10 is shown positioned on either side of a PFO track (referenced as PFO in the Figures) with a portion of the device 10 passing through the PFO track, after delivery from a delivery system. The PFO track can be seen more clearly in FIG. 2, which shows a catheter disposed in the PFO track between the septum primum (SP) and septum secundum (SS). As shown in FIG. 1, closure device 10 includes a left atrial anchor 12 positioned in the LA, a right atrial anchor 14 positioned in the RA, and an elongate member in the form of a tether 16 connecting the anchor structures.

As embodied herein and shown in FIGS. 1 and 11, closure device 10 includes left atrial anchor 12 connected to tether 16. FIG. 11 shows tether 16 extending through and connecting to right atrial anchor 14 via a releasable fixation mechanism 30 (which is fixed to right atrial anchor 14). When releasable fixation mechanism 30 is not fixed, right atrial anchor 14 is moveable along tether 16. As shown in FIG. 11, releasable fixation member 30 engages tether 16, which extends through right atrial anchor 14 on a side of right anchor 14 which does not face left anchor 12. Although it is preferable that left atrial anchor 12 is permanently attached to tether 16, it is possible that left atrial anchor 12 may also be attached to tether 16 by a device similar to releasable fixation mechanism 30.

In one embodiment, tether 16 is formed of a multifilar braided polymeric material. Suitable materials include, but are not limited to, multifilament yarns of ultra-high molecular weight polyethylene (UHMWPE) such as SPECTRA or DYNEEMA. Other suitable materials include liquid crystal polymer (LCP) such as VECTRAN, polyester, or other high strength fibers. Other suitable materials of sufficient strength and flexibility may be used for tether 16.

Releasable fixation mechanism 30 is preferably spring-loaded and is shown in FIG. 11 in a fixed condition on tether 16, i.e., fixation mechanism 30 has fixed tether 16 to anchor 14. Releasable fixation mechanism 30 includes two oppositely directed piercing pins 32, which are adapted to penetrate and pierce tether 16. Each piercing pin 32 includes a spring portion 32*a* which connects to a housing 31 and the corresponding piercing pin 32. In the embodiment shown, housing 31 connects to an anchor attachment hub 36, which in turn connects to anchor 14, as will be described below.

Piercing pin 32 has a sharpened end and is oriented generally orthogonal to tether 16. Spring portion 32*a* is connected to housing 31 such that the natural, unbiased position of spring portion 32*a* forces piercing pin 32 through tether 16. Piercing pins 32 are illustrated as passing completely through tether 16, but it is contemplated that pins 32 may pass only partially into tether 16.

Piercing pins 32 cooperate with a piercing collar 34 that is attached to housing 31. Collar 34 has an internal passage which is somewhat larger than tether 16. In the embodiment shown, collar 34 also has two passageways, one for each piercing pin 32, through which piercing pins 32 pass. Once piercing pins 32 have passed into (and potentially through) tether 16, piercing pins 32 securely lock tether 16 relative to fixation mechanism 30 and thus to right atrial anchor 14. Piercing collar 34 also holds tether 16 in place if piercing pins 32 are desired to be extracted from tether 16, as will be described later.

Piercing pins 32 are preferably formed of an elastic metal with spring characteristics. Suitable materials include but are not limited to stainless steel, nickel-titanium, ELGILOY, or MP35N. Housing 31 is preferably a thin walled tube formed of a biocompatible metal or polymer. The releasable fixation mechanism 30 illustrated in FIG. 11 is exemplary only, and other embodiments of a releasable fixation mechanism suitable to fix tether 16 to anchor 14 are contemplated, some of which will be described below.

Figure 12:
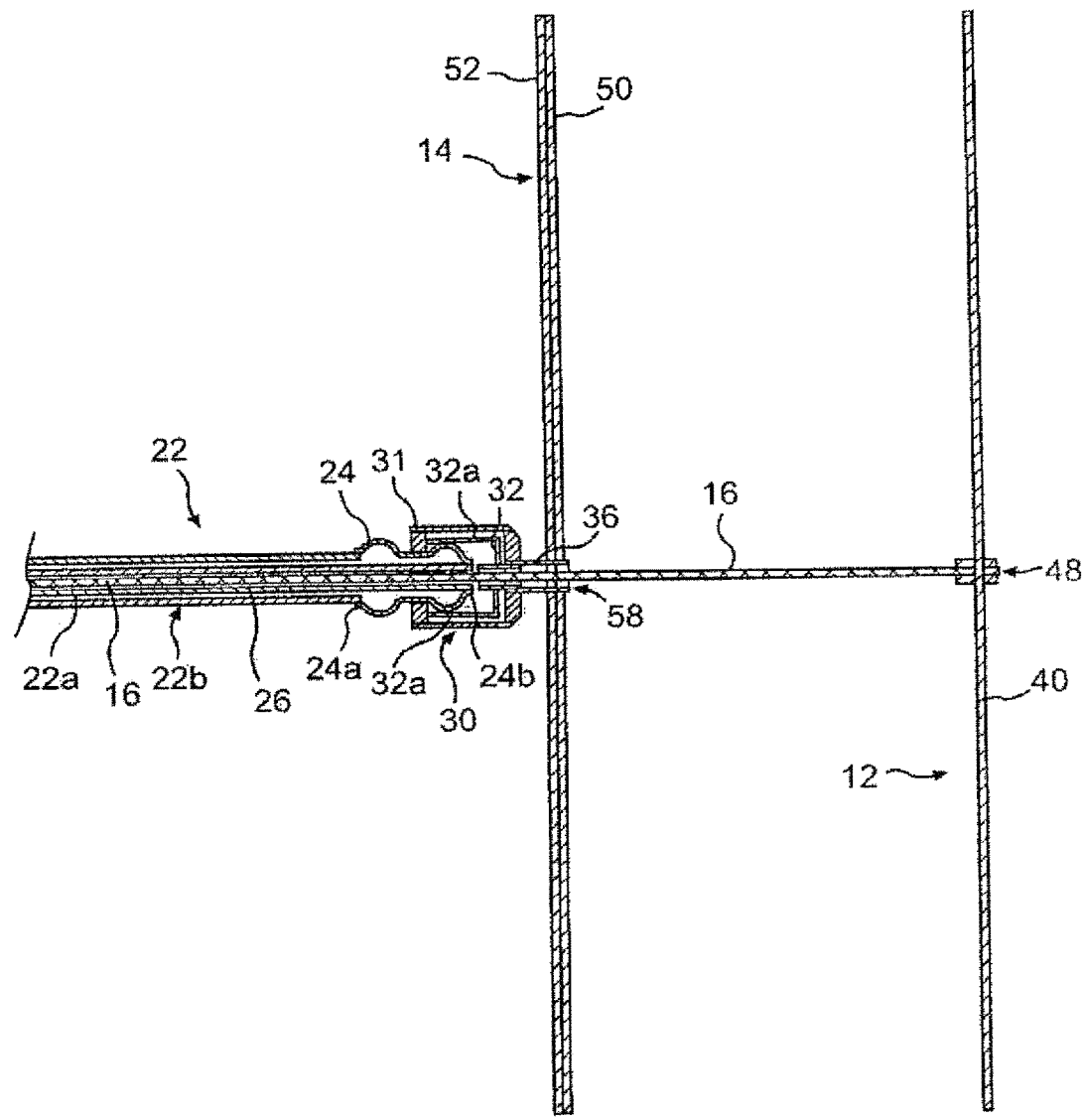
FIG. 12 is a cross-sectional side view of the closure device of FIG. 11 with a positioning catheter (shown in cross section) engaging a fixation mechanism (also shown in cross section), according to an embodiment of the present invention.

FIG. 12 illustrates the operation of releasable fixation mechanism 30 shown in FIG. 11. In FIG. 12, a right atrial anchor positioning catheter (RPC) 22 is engaged with right atrial anchor 14, such that right atrial anchor 14 is not yet secured to tether 16. RPC 22, as embodied herein and shown in FIG. 12, includes an inflatable balloon 24 which, when inflated, engages releasable fixation mechanism 30, allowing right atrial anchor 14 to be moved relative to tether 16. RPC 22 includes a lumen 26 which allows for inflation and deflation of balloon 24. A proximal end 24*a* of balloon 24 is attached to a distal end of an outer tube 22*b* of RPC 22, whereas a distal end 24*b* of balloon 24 is attached to the distal end of an inner tube 22*a* of RPC 22. The inner and outer tubes 22*a*, 22*b* of RPC 22 define lumen 26.

Balloon 24 is shown in FIG. 12 in its inflated condition. Balloon 24 may be formed in the dumbbell shape, as, shown, to facilitate engagement with releasable fixation mechanism 30. As shown, when balloon 24 is inflated, a distal portion of dumbbell shaped balloon 24 presses against spring portions 32*a*, a proximal portion of balloon 24 expands without contacting any surface, and a middle waist portion of balloon 24 presses against housing 31, limiting expansion of that waist portion. The distal portion of balloon 24 forces piercing pins 32 outward from tether 16. This is done by balloon 24 pressing outward against spring portions 32*a* of piercing pins 32. Once a desired position for right atrial anchor 14 with respect to left atrial anchor 12 and tether 16 is established, balloon 24 is deflated, which allows piercing pins 32 to penetrate tether 16, fixing anchor 14 with respect to tether 16. If it is desired to re-position right atrial anchor 14 after fixing, RPC 22 is advanced along tether 16 to re-engage releasable fixation mechanism 30. Balloon 24 is re-inflated, extracting pins 32 from tether 16, and allowing for re-positioning of right atrial anchor 14 relative to tether 16.

RPC 22 described and illustrated with respect to FIG. 12 is only exemplary, and other catheter structures which may interact with a releasable fixation mechanism are contemplated. For example, catheter devices with alternative mechanical expansion structures for releasably engaging the fixation mechanism may be used.

Figure 11A:
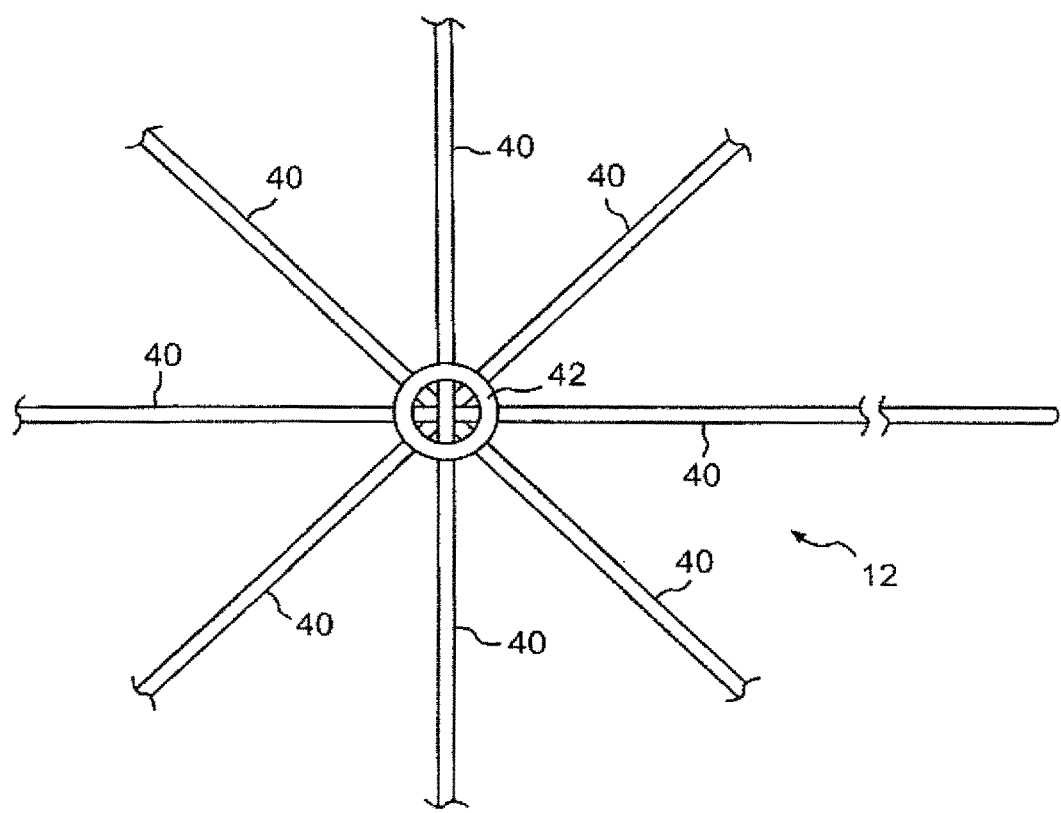
FIG. 11A is a partial plan view of a left atrial anchor of the closure device of FIG. 11 taken along line A-A, according to an embodiment of the present invention.

FIG. 11A illustrates an embodiment of left atrial anchor 12 and its connection to tether 16. As embodied herein and shown in FIG. 11A, anchor 12 includes one or more arms 40, which preferably extend across an anchor attachment hub 42. Attachment hub 42 is tubular, preferably made of a biocompatible metallic or polymeric material, and includes radially oriented passageways through which arms 40 extend. FIG. 12 shows one such radial passageway through which an arm 40 extends. Arms 40 may be further secured to attachment hub 42 by suitable means such as welding, brazing, adhesive bonding, or any other suitable method of securing arms 40 to hub 42. Anchor attachment hub 42 also defines a longitudinal lumen 48 through which tether 16 extends, as shown in FIG. 11. Each arm 40 extends generally orthogonally through the tether 16, passing through the braid structure of tether 16 and fixing the left atrial anchor to tether 16. FIG. 11A illustrates anchor 12 having four arms, however any number of arms may be used, preferably from one to six. While not shown in FIG. 11, arms 40 of this embodiment would be spaced longitudinally relative to one another along the length of tether 16, at least in the region of the anchor attachment hub, i.e., no two arms would be located at exactly the same point on the tether 16.

Although arms 40 preferably pass through hub 42, in an alternative arrangement arms 40 may not actually pass though hub 42, i.e., they may extend radially from hub 42. Additionally, it is possible that instead of arms 40, the anchors 12, 14 may comprise spiral structures, flat braided structures, or webs. Any structure of sufficient size and shape to hold the septum primum (SP) in contact with the septum secundum (SS) to close the PFO may be used.

Arms 40 are preferably fabricated of metallic wire, such as stainless steel, nickel-titanium, ELGILOY, or MP35N. In the case of nickel-titanium, the wires may be used in either a super-elastic mode, whereby the wires deploy due to the super-elastic properties of this alloy, or they may be used in a thermal-transforming mode. In the thermal-transforming mode, the wires may be chilled prior to deployment, for example by the introduction of chilled saline in the delivery assembly, and subsequently warmed by exposure to the blood, once guide catheter 20 (or a delivery sheath) is withdrawn.

As shown in FIG. 11A, arms 40 may be straight. Alternatively, arms 40 may be formed to present a concave-shaped anchor to the atrial wall. The anchor 12 and its arms 40 then will conform to lay flat and apposed to the surface of the atrial wall once tensioned by tether 16. It is preferable for arms 40 to lie on or close to the atrial wall surface once fully positioned, as this will facilitate tissue growth over arms 40, and minimize thrombus formation and subsequent embolization of thrombi. To further assist in arms 40 becoming rapidly endothelialized and grown into the atrial wall, arms 40 may be individually coated with a material to accelerate this ingrowth, such as expanded PTFE or a woven polyester. Arms 40, together with any desired coating, may further be coated with a non-thrombogenic Material such as heparin. All exposed surfaces of the closure device, including the full length of tether 16, may include such coatings.

To minimize frictional forces between a guide catheter 20 (or delivery sheath) and the undeployed anchors, as well as minimizing tissue trauma during deployment, the ends of arms 40 are preferably rounded (as shown by the right-hand arm in FIG. 11A). The ends of arms 40 also may include small loops to receive sutures, for example, for suturing to a covering of the anchor 12. The overall length of the arms (which will correspond to the diameter of the anchor) will depend on the particular anatomy to be treated, but will preferably range from about 3-50 mm for septal closure applications including PFO closure. Arms 40 need not extend an equal distance from the attachment hub. Depending on the location of the PFO relative to remainder of the left atrium, it may be desirable to have some of arms 40 extend asymmetrically from the attachment hub 42, for example, longer towards the inferior direction. Also, while left atrial anchor 12 is shown in FIG. 11A without a fabric covering spanning the arms, it is anticipated that in some instances it may be beneficial to incorporate such a covering, similar to that described below in connection with right atrial anchor 14 shown in FIG. 11C.

Figure 11B:
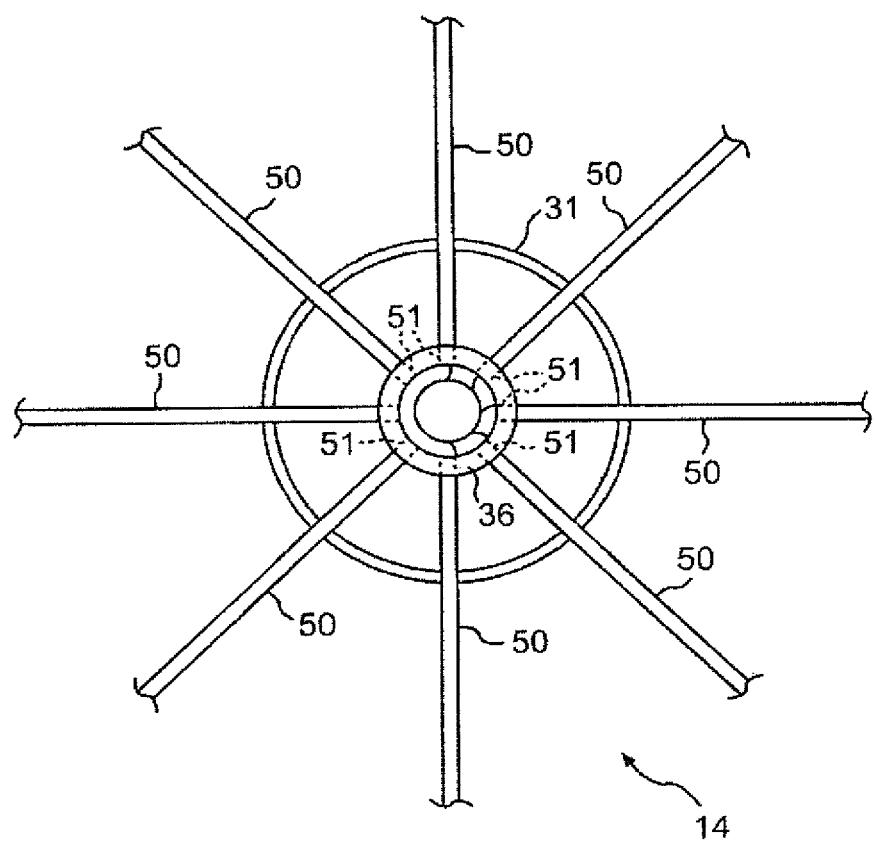
FIG. 11B is a partial plan view of a right atrial anchor of the closure device of FIG. 11 taken along line B-B, shown without a covering, according to an embodiment of the present invention.

FIG. 11B illustrates an embodiment of right atrial anchor 14 and its connection to anchor attachment hub 36. Tether 16 and the fabric that covers anchor 14 are not shown in FIG. 11B. As embodied herein and shown in FIG. 11B, right atrial anchor 14 includes one or more arms 50 which extend through anchor attachment hub 36. Attachment hub 36 for right atrial anchor 14 is similar to that for left atrial anchor 12 and defines a longitudinal lumen 58 (see FIG. 11) through which tether 16 extends and radially oriented passages 51 in its wall through which arms 50 extend. Unlike left atrial anchor 12, arms 50 do not extend through tether 16. Instead, arms 50 are formed to curve around tether 16 and follow the inner surface of anchor attachment hub 36, as shown in FIG. 11B. FIG. 11B also illustrates four arms, but a larger or smaller number of arms may be used, preferably from one to six arms. Arms 50 may be formed straight (away from hub 36), or with a concave shape, as described in connection with left atrial anchor 12. Preferred materials include those described for left atrial anchor arms 40. The overall length of arms 50 (which will correspond to the diameter of anchor 14) will depend on the particular anatomy to be treated, but will preferably range from about 3-50 mm for septal closure applications including PFO closure. In some instances, left atrial anchor arms 40 are the same length as right atrial anchor arms 50, and in others they may be different, e.g. shorter than right atrial anchor arms 50. This will depend on the anatomy of the heart.

Figure 11C:
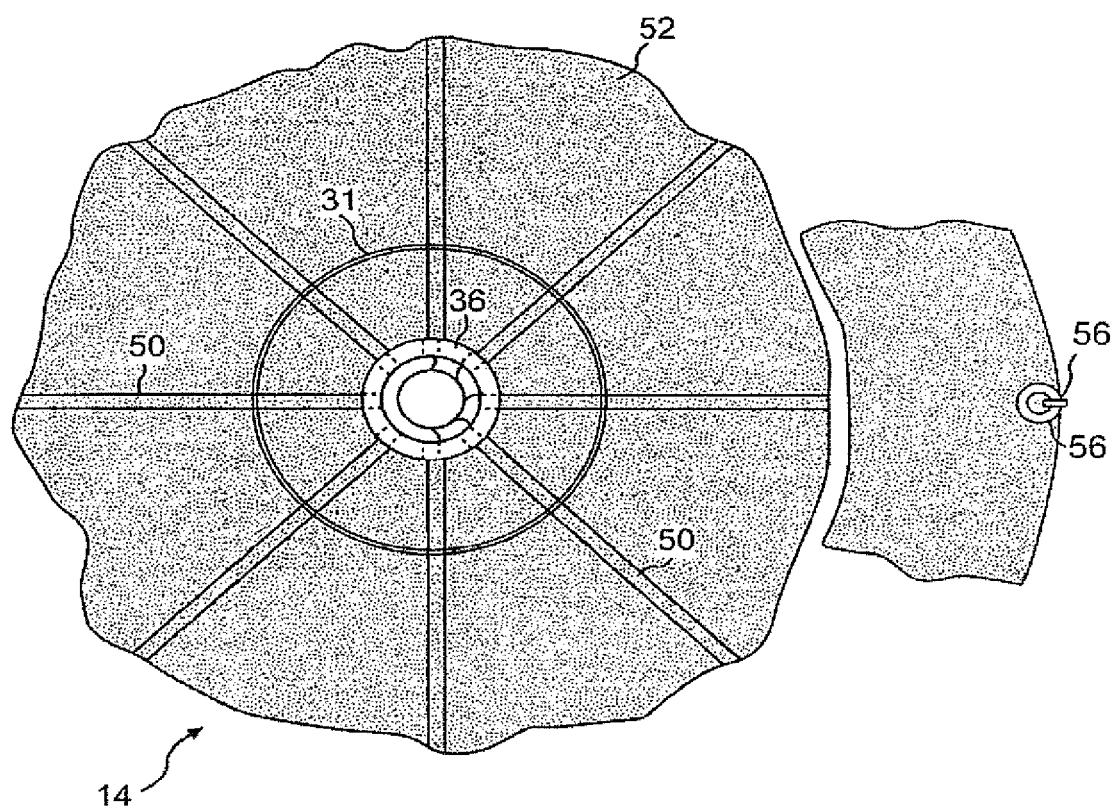
FIG. 11C is a partial plan view of the right atrial anchor of FIG. 11B shown with a covering, according to an embodiment of the present invention.

Right atrial anchor 14 preferably includes a fabric or other membrane covering that span between arms 50. This covering, represented in FIG. 11C as reference numeral 52, serves to ensure a hemodynamic sealing of the PFO. The covering 52 is preferably formed of a single sheet, with a hole for surrounding anchor attachment hub 36, and is preferably positioned on the arms 50 such that it faces the septum. Suitable materials for covering 52 include, but are not limited to, woven or knit polyester fabric, or ePTFE. Preferably, covering 52 has a porosity which will encourage rapid tissue ingrowth. Covering 52 may additionally include a coating, for example, a non-thrombogenic material such as heparin. Covering 52 may be attached to arms 50 of right atrial anchor 14 by suitable means, such as suturing. As shown in FIG. 11C, arm 50 may have a loop 54 formed at each of its ends, creating eyelets for a suture 56 to connect arm 50 to covering 52.

Additional sutures may be incorporated along the length of arms 50. Although not preferred and not discussed with respect to left atrial anchor 12, it is possible to include a covering attached to arms 40 of left atrial anchor 12.

Figure 13:
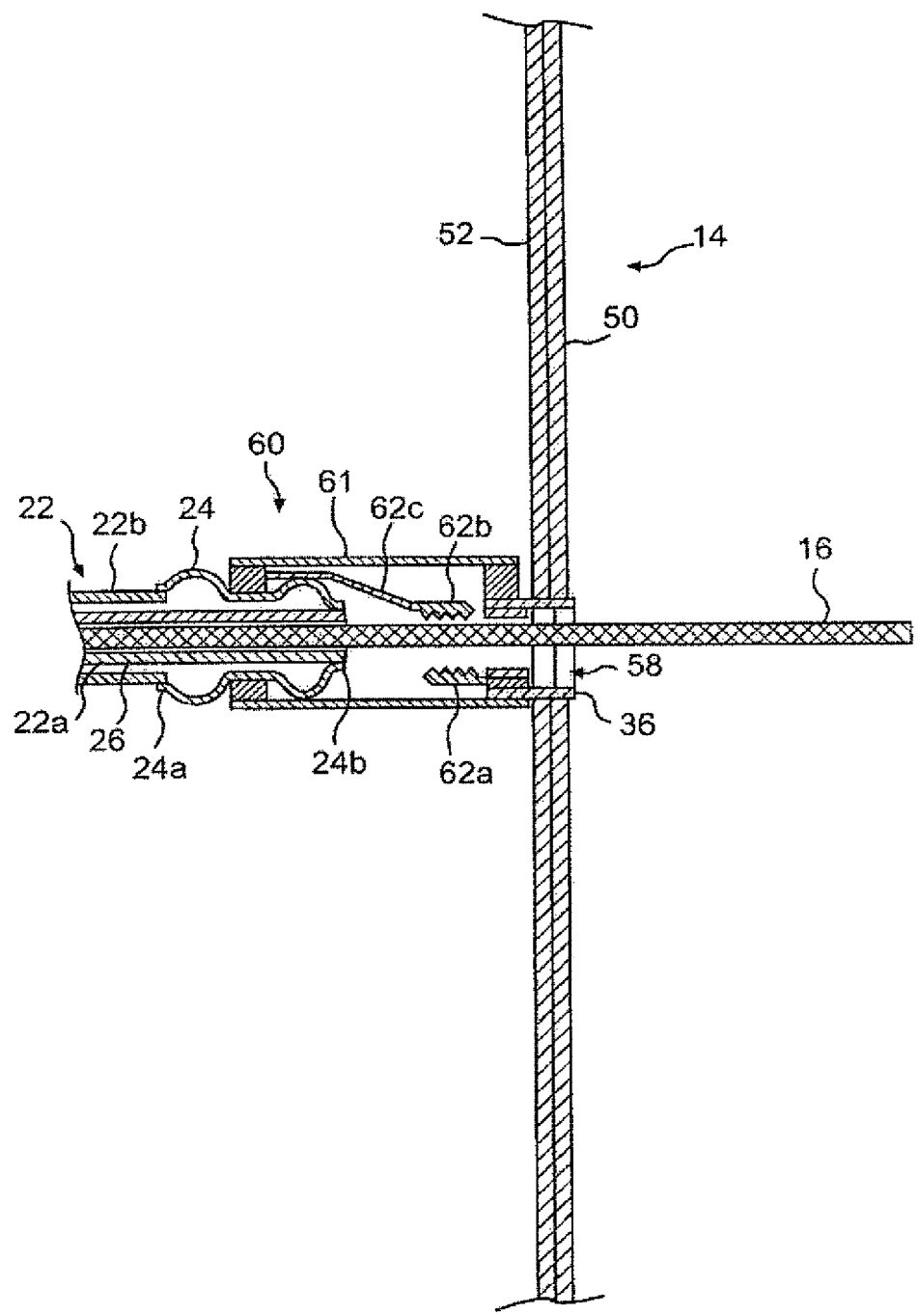
FIG. 13 is a cross sectional side view of the positioning catheter of FIG. 12 engaging another embodiment of a fixation mechanism according to the present invention.

FIG. 13 illustrates an alternative embodiment of a releasable fixation mechanism. A releasable fixation mechanism 60 operates in conjunction with right atrial positioning catheter RPC 22 in a manner similar to that described above. As in the prior described embodiment, anchor attachment hub 36 connects to a housing 61 of mechanism 60. Housing 61 contains a gripping structure, preferably with two grips, a fixed grip 62a and a movable grip 62b. Fixed grip 62a is connected to housing 61 and has a rough surface with sharpened teeth-like projections. Movable grip 62b has a spring portion 62c connected to housing 61. Grip 62b also includes sharpened teeth-like projections. When inflated, balloon 24 holds movable grip 62b away from tether 16, but when balloon 24 is deflated, spring portion 62c forces movable grip 62b against tether 16, and also forces tether 16 against fixed grip 62a. In this way, tether 16 fixedly connects to right atrial anchor 14.

Figure 16:
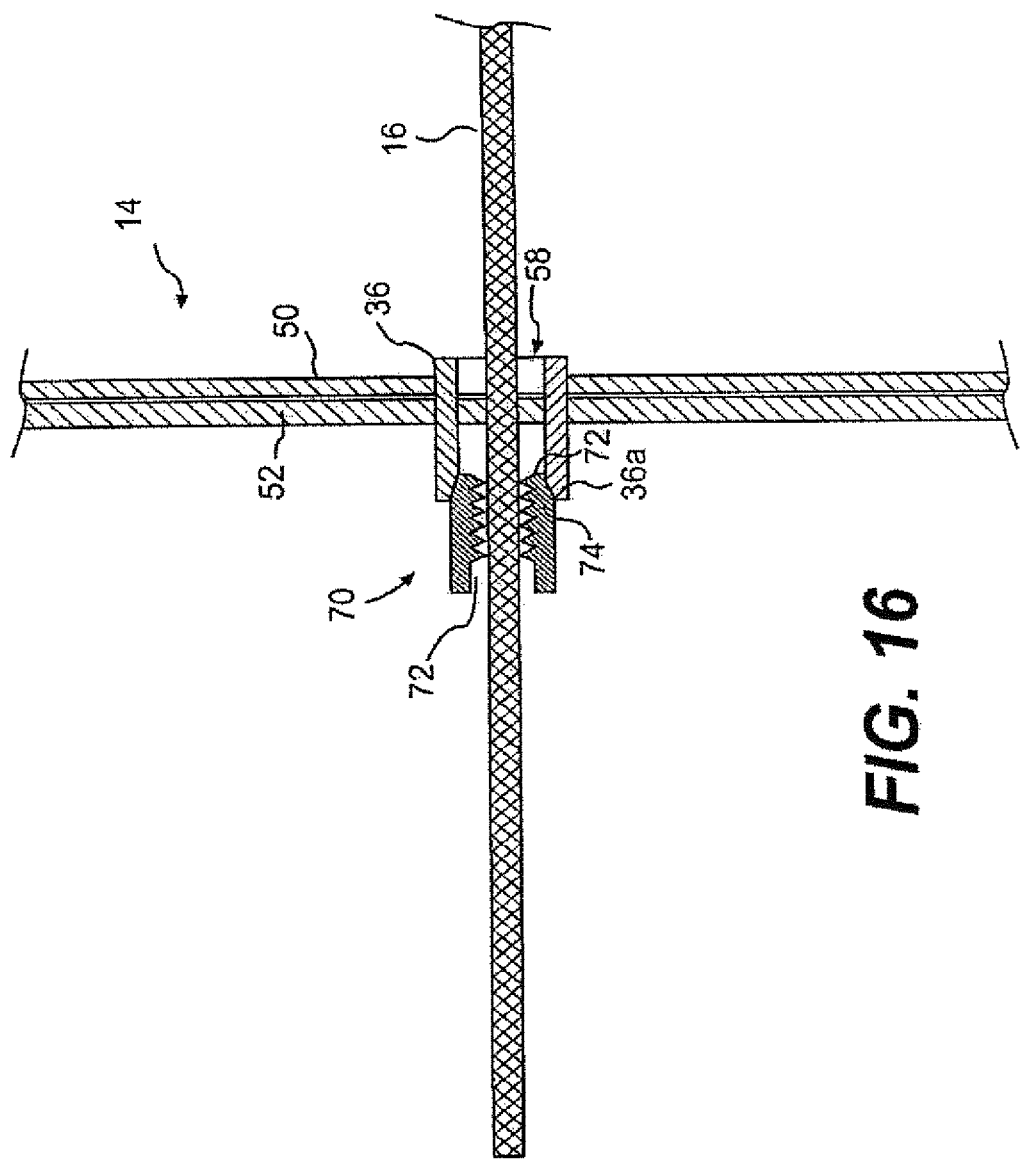
FIG. 16 is a partial cross sectional view of another embodiment of a fixation mechanism engaging a right atrial anchor, according to the present invention.

In another embodiment according to the present invention, the closure device 10 need not incorporate a releasable fixation mechanism such as those described above. Instead, other structures may be used to fix right anchor 14 to tether 16. In such an embodiment, as illustrated in FIG. 16, anchor 14 is connected to anchor attachment hub 36, as in the embodiments described above. Also as in the prior embodiments, once right atrial anchor 14 is deployed, it is not yet fixed to tether 16. When right atrial anchor 14 is in its desired position, a locking element 70 is advanced along tether 16 towards anchor 14. Element 70, when it reaches hub 36, will secure to both tether 16 and anchor attachment hub 36. Locking element 70 is not necessarily releasable, and as such would be permanent. Locking element 70 may be moved distally by any suitable actuation mechanism known in the art that extends through a delivery assembly to its proximal end outside of the patient.

Locking element 70 is preferably tubular and includes a number of projecting grips 72. These grips 72 may be oriented in a ratchet-like manner (not shown) such that locking element 70 can be advanced distally along tether 16, but will resist proximal movement. Alternately, locking element 70 can be positioned in the desired location on tether 16, and swaged down to bite into the surface of tether 16. As a further alternative, locking element 70 may have an outer surface 74 which is tapered to engage with a tapered inner surface 36a of anchor attachment hub 36 in a wedge-like manner, as shown in FIG. 16. As locking element 70 is pushed into anchor attachment hub 36, the gripping surface 72 is forced inward to bite into tether 16.

While not shown, locking element 70 could also be used in conjunction with the embodiments above which utilize a releasable fixation mechanism. As such, locking element 70 would provide extra security in the fixation of right atrial anchor 14 to tether 16.

Figure 14:
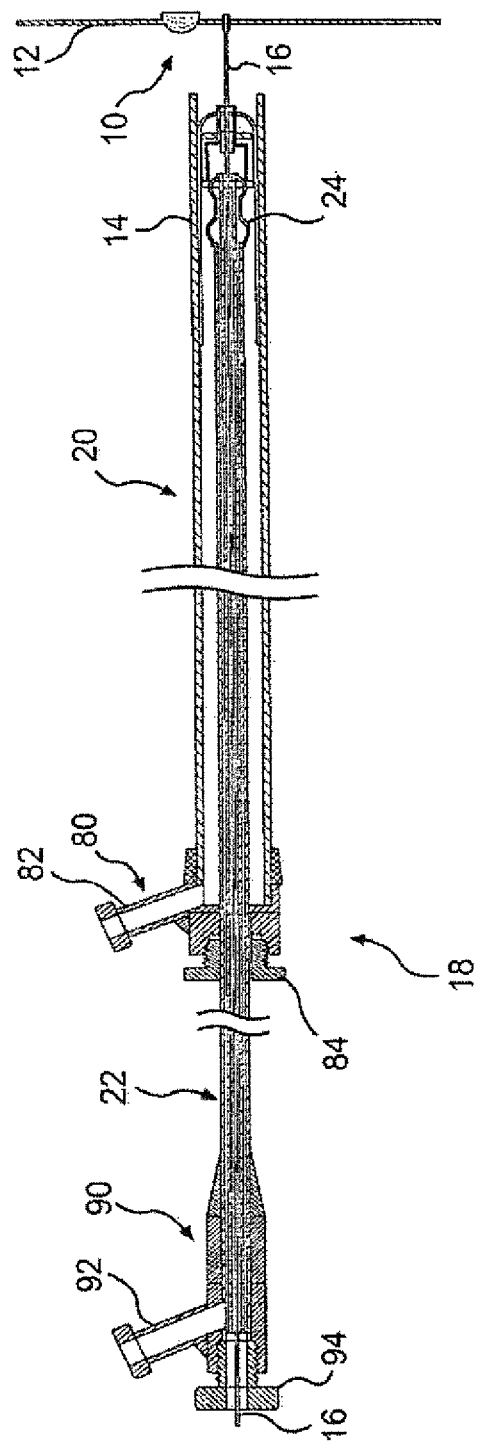
FIG. 14 is a cross sectional side view of a delivery system, including a guide catheter and a positioning catheter, according to an embodiment of the present invention.

FIG. 14 shows the closure device 10 positioned relative to an embodiment of a delivery apparatus 18. In FIG. 14, left atrial anchor 12 is shown deployed from delivery apparatus 18, while right atrial anchor 14 is shown in a collapsed, undeployed state within delivery apparatus 18. Delivery apparatus 18 may include a guide catheter 20 and right atrial positioning catheter (RPC) 22. Although not shown, guide catheter 20 may have a pre-formed curve near its distal end. Guide catheter 20 can be any suitable, conventional guide catheter. A suitable, exemplary guide catheter is known as "Mullins" guide catheter, sold commercially by Cook. Connected to the proximal end of guide catheter 20 is a conventional Y-adaptor 80. A side arm 82 of Y-adaptor 80 allows fluid communication with the lumen of guide catheter 20. Y-adaptor 80 also contains a touhy borst seal 84, through which RPC 22 extends.

As described earlier, RPC 22 includes balloon 24 for engaging right atrial anchor 14. Therefore RPC 22 is provided with a manifold 90 at a proximal end which includes a port 92 in fluid communication with balloon 24. Manifold 90 may further include a touhy borst seal 94, through which tether 16 extends.

Figure 15:
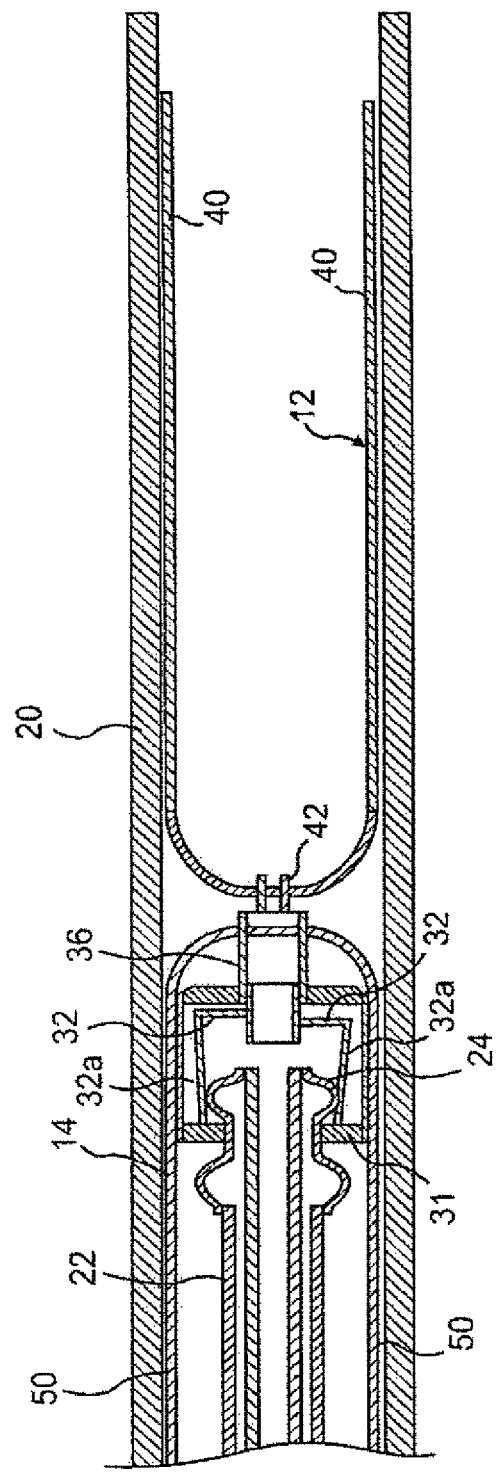
FIG. 15 is a cross sectional side view of a closure device and a positioning catheter positioned in a guide or delivery catheter prior to deployment in a heart, according to an embodiment of the present invention.

As mentioned, FIG. 14 depicts closure device 10 after left atrial anchor 12 has been deployed. However, prior to closure device 10 being in this state, guide catheter 20 would be delivered by conventional techniques to the site of the PFO. Such conventional techniques may include the temporary use of a guide wire (not shown). Closure device 10 then would be positioned within the lumen of guide catheter 20, by suitable techniques, and advanced toward the distal end of guide catheter 20, into a position depicted in FIG. 15. As shown in FIG. 15, right atrial anchor 14 is folded in a proximal direction, while left atrial anchor 12 is folded in a distal direction within guide catheter 20. More specifically, arms 40 of left atrial anchor 12 are folded so as to extend in a distal direction, whereas arms 50 of right atrial anchor 14 are folded so as to extend in a proximal direction. This is a preferred position of the arms in a delivery position. Alternatively, it is possible that the arms of anchors 12 and 14 are folded to extended in the same direction, either distal or proximal, or the anchor may be disposed with arms 40 of left atrial anchor 12 folded to extend in a proximal direction and arms 50 of right atrial anchor 14 folded to extend in a distal direction.

When it is desired to deploy left atrial anchor 12, right atrial positioning catheter 22 is advanced relative to guide catheter 20, or guide catheter 20 is withdrawn relative to the RPC 22, or both. Since RPC 22 is engaged with right atrial anchor 12, the forces required for advancement of left atrial anchor 14 can be compressively transferred to abutting left atrial anchor 12.

FIGS. 2-10 show sequential steps for delivery of closure device 10, according to one aspect of the invention. At the level of the longitudinal section shown in FIG. 1, the inferior vena cava (IVC) is not shown. In an embodiment, a delivery system is passed through the IVC to gain access to the RA and PFO. Other methods of percutaneously, minimally invasively, or more directly obtaining access to the RA and PFO are within the scope of the invention. As embodied herein and shown in FIG. 2, a delivery assembly 18 including a guide catheter 20 is advanced to and through the PFO track and into the LA. Delivery assembly 18 is shown in detail in FIG. 14. In addition to closure device 10, additional delivery components, such as a delivery sheath or positioning catheter, may be included within the delivery assembly, as will be described below.

Figure 2:
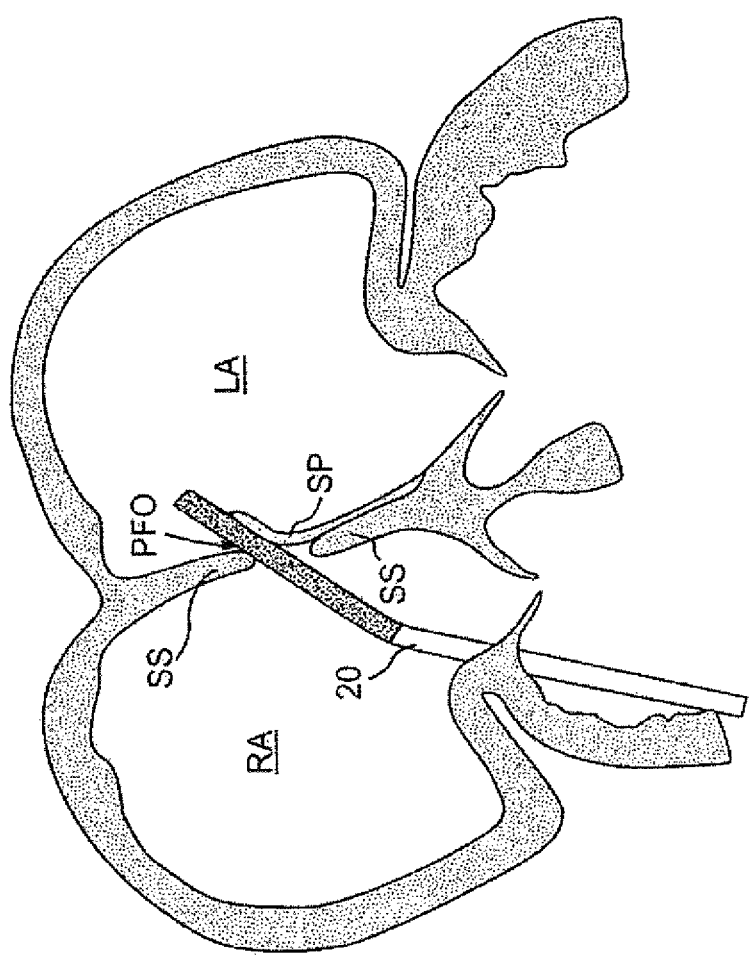
FIG. 2 is a delivery system guide catheter inserted through a PFO and into the left atrium, according to an embodiment of the present invention.

As embodied herein and shown in FIG. 2, in a method of delivery of closure device 10, guide catheter 20 is positioned through the PFO track with the use of a conventional guide wire (not shown). After positioning of guide catheter 20 into the LA, the guide wire may be removed. Closure device 10, in a collapsed state as shown in FIG. 15 and as will be described below, and any delivery components are advanced within guide catheter 20 until closure device 10 is near a distal end of guide catheter 20.

Figure 3:
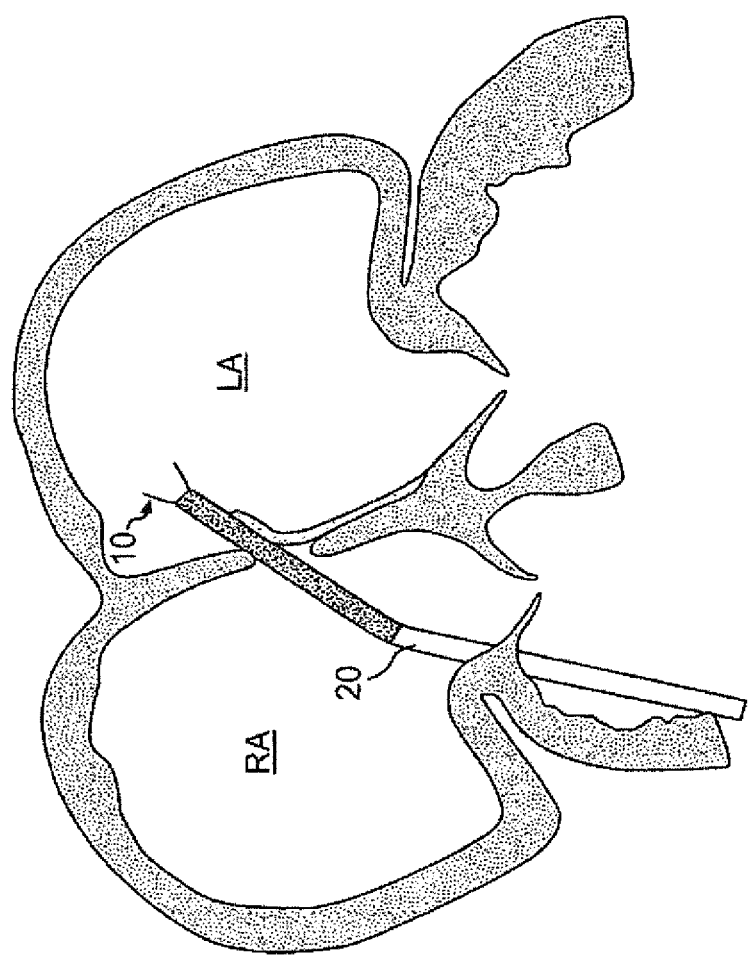
FIG. 3 is a left atrial anchor of closure device of FIG. 1 being advanced out of the delivery guide catheter, according to an embodiment of the present invention.

Then, as shown in FIG. 3, closure device 10 is advanced out of the distal end of guide catheter 20. The advancement is accomplished by relative movement between guide catheter 20 and closure device 10 and its delivery components. Preferably, the advancement is accomplished by maintaining the position of guide catheter 20, and pushing delivery components in a distal direction to push closure device 10 out of a distal end of guide catheter 20.

Figure 4:
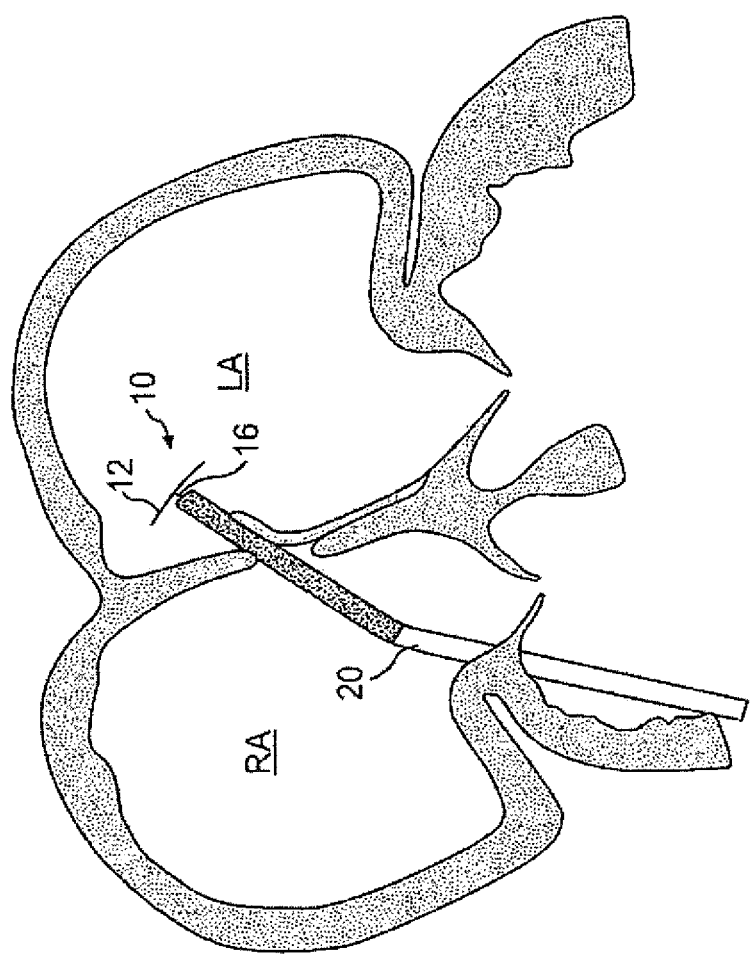
FIG. 4 is a left atrial anchor of the closure device of FIG. 1 advanced out of the delivery guide catheter, according to an embodiment of the present invention.

While guide catheter 20 and delivery components are within the left atrium, only left atrial anchor 12 is deployed from guide catheter 20. FIG. 4 shows left atrial anchor 12 fully deployed from guide catheter 20 in the LA. FIG. 14 also shows the delivery assembly with left atrial anchor 12 deployed. Tether 16 extends from anchor 12 into the delivery assembly. As discussed above, left atrial anchor 12 and right atrial anchor 14 are preferably self-expanding structures, expanding through a mechanical or thermal shape change, for example. Also at this point, right atrial anchor 14 remains within the delivery assembly in a collapsed state.

Figure 5:
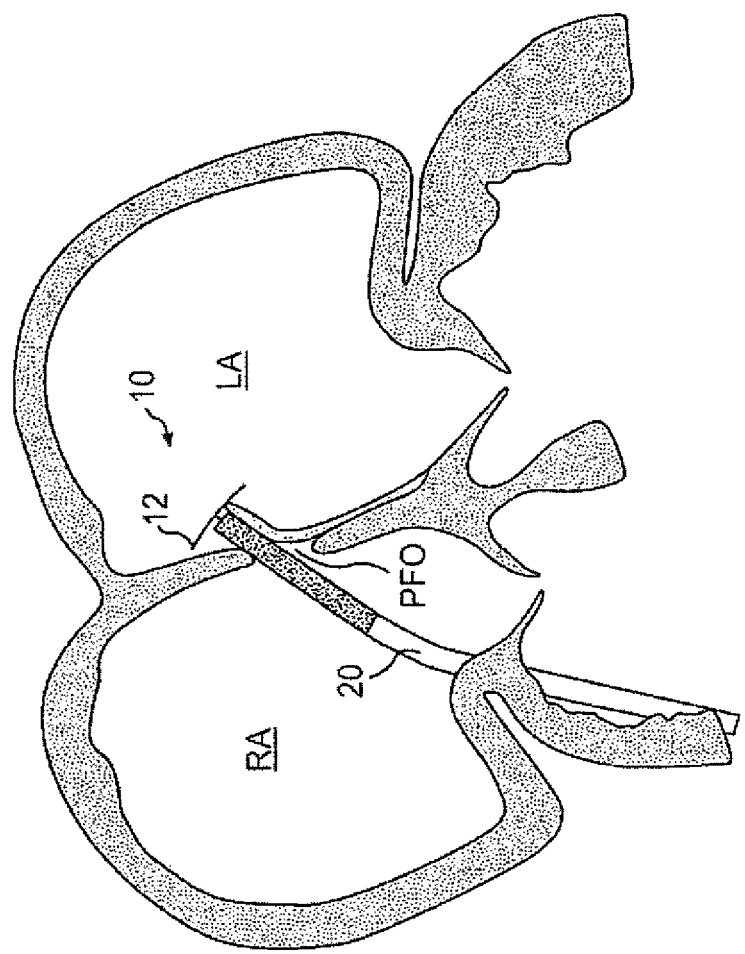
FIG. 5 is the left atrial anchor of FIG. 4 being pulled towards the PFO, according to an embodiment of the present invention.

In the next step of an embodiment of the delivery method, left atrial anchor 12 is pulled against the opening of the PFO, as shown in FIG. 5. This is done by the user pulling guide catheter 20 and other delivery components proximally. As guide catheter 20 is withdrawn proximally, left atrial anchor 12 will seat naturally against the septal wall, as shown in FIG. 6.

Figure 6:
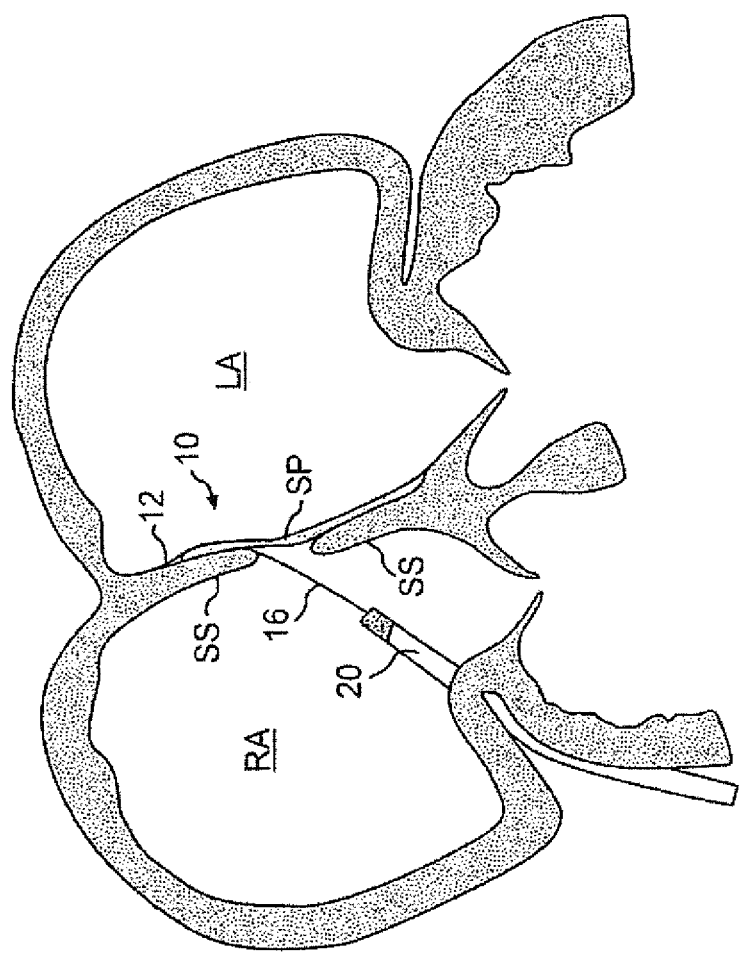
FIG. 6 is the delivery guide catheter pulled proximally into the right atrium and the left atrial anchor seated against a septal wall, according to an embodiment of the present invention.

As shown in FIG. 6, a significant portion of the PFO track (specifically the portion of the track between the superior portion of the septum primum and septum secundum) runs along and roughly parallel with the septal wall. A feature of closure device 10 according to this embodiment is that left atrial anchor 12 and tether 16 are flexibly connected, and tether 16 is itself preferably flexible, to allow tether 16 to extend through the PFO track, while left atrial anchor 12 remains significantly apposed to the left ventricular surface. Tether 16 is able to extend from left atrial anchor 12 at an obtuse angle. In many instances, left atrial anchor 12, with tension applied from tether 16, may mechanically close and thereby seal the PFO by bringing the septum primum (SP) into sealing contact with the septum secundum (SS). The effectiveness of this seal can be tested at this time by conventional techniques, such as contrast visualization, or a Valsalva maneuver combined with injection of bubbles, visualized with transesophageal ultrasound or intracardiac ultrasound. If the seal is ineffective, closure device 10 can be removed as described later, and exchanged for a different device, for example, a device including a covering on arms 40 of left atrial anchor 12. Alternatively, the device 10 can be repositioned as described below.

Figure 7:
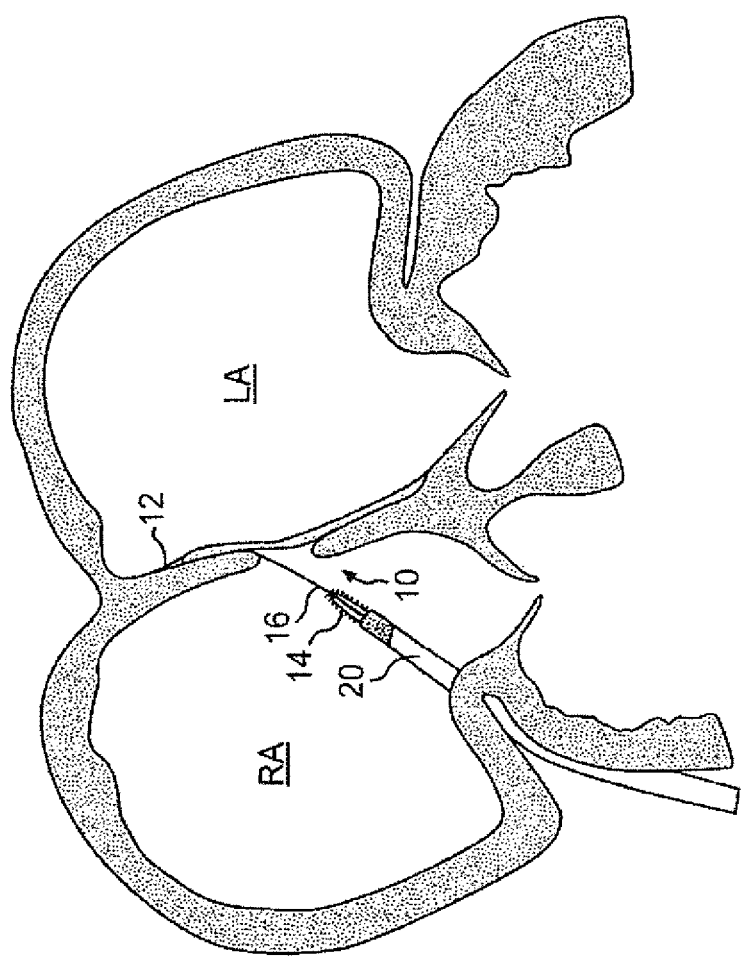
FIG. 7 is a right atrial anchor of the closure device of FIG. 1 being extended from the delivery guide catheter, according to an embodiment of the present invention.

Once left atrial anchor 12 is positioned, right atrial anchor 14 may be deployed. As shown in FIG. 7, initial deployment of right atrial anchor 14 is preferably performed with the delivery assembly and the collapsed right atrial anchor 14 withdrawn sufficiently away from left atrial anchor 12 and the right atrial septal wall, so that right atrial anchor 14 does not impinge on the wall when it initially expands. Positioning right atrial anchor 14 in this position prior to deployment also assures that right atrial anchor 14 will not inadvertently deploy in the PFO track or the left atrium. Because right atrial anchor 14 is not permanently attached to tether 16, anchor 14 is free to be positioned in such a location.

Figure 8:
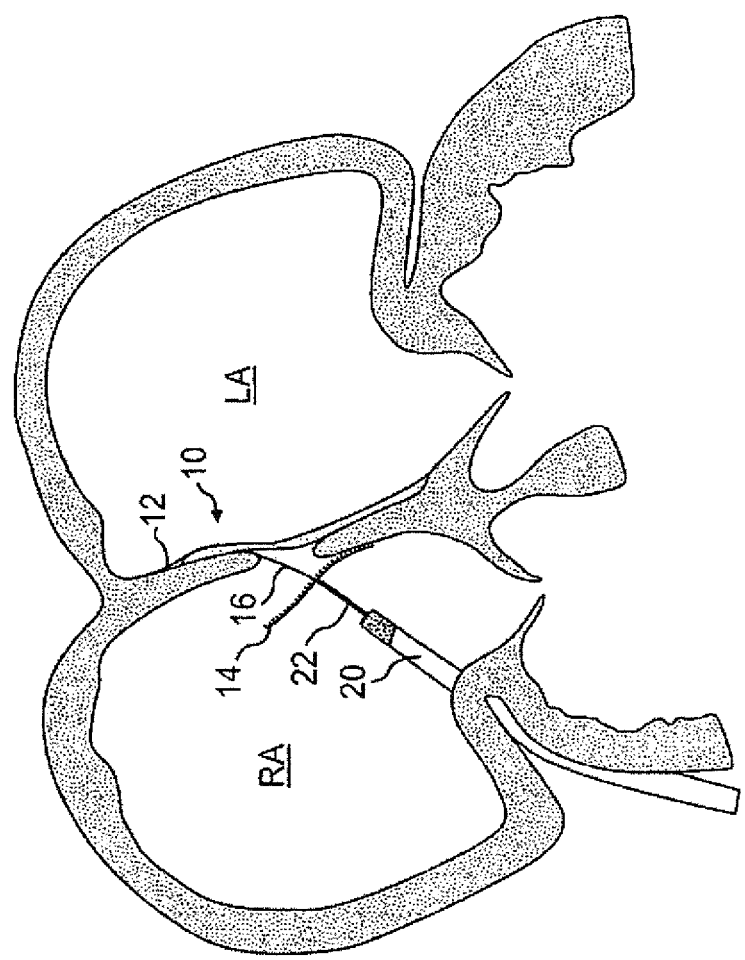
FIG. 8 is the right atrial anchor deployed from the delivery guide catheter, according to an embodiment of the present invention.
Figure 9:
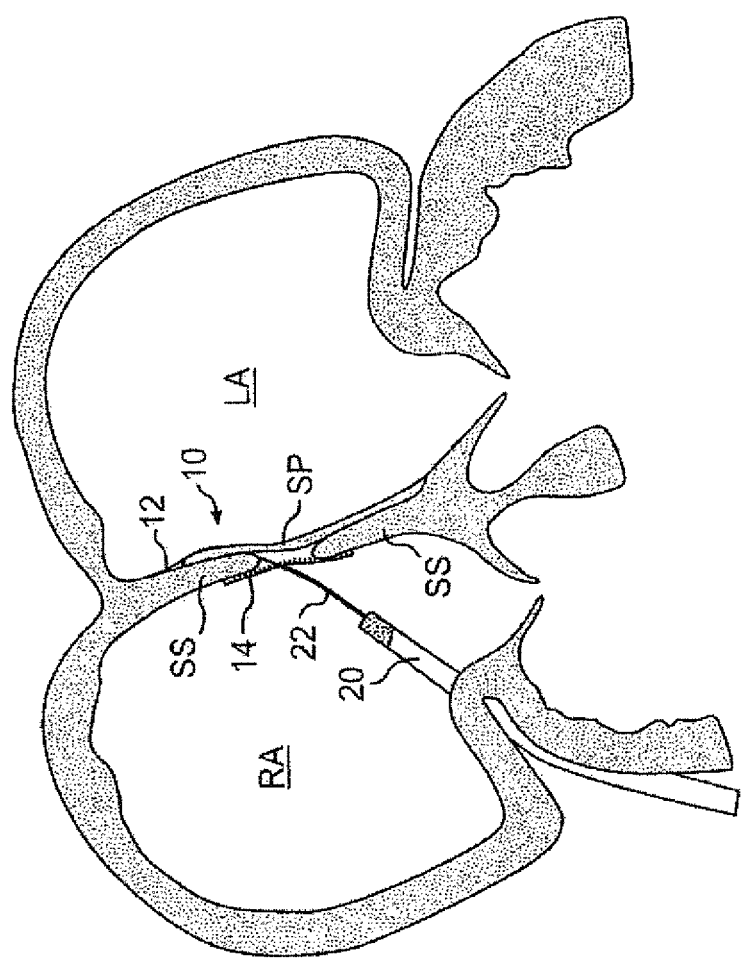
FIG. 9 is the right atrial anchor advanced to contact the septal wall, according to an embodiment of the present invention.

Right atrial anchor 14 is temporarily connected to a right atrial anchor positioning catheter (RPC) 22, as shown in FIGS. 8 and 9 and described in detail below. Deployment of right atrial anchor 14 is accomplished by relative movement of guide catheter 20 and RPC 22, either by grasping a proximal end of RPC 22 and withdrawing guide catheter 20, or by grasping guide catheter 20 and advancing RPC 22. This relative movement results in full deployment of right atrial anchor 14 within the right atrium RA, as shown in FIG. 8. At this stage of the delivery method, tether 16 passes through right atrial anchor 14 and preferably extends continuously through guide catheter 20 to the proximal end of the delivery assembly 18. Right atrial anchor 14 is not yet fixed to tether 16 and instead is connected to RPC 22. Preferably, tether 16 also extends through RPC 22.

In the next step of this embodiment of a closure device delivery method, right atrial anchor 14 is advanced into contact with the right atrial septal wall, as shown in FIG. 9. This is accomplished by advancing right atrial anchor 14 and RPC 22 along tether 16 until right atrial anchor 14 is in a desired position relative to left atrial anchor 12, the septal wall, and the PFO, and has a desired amount of tension on left atrial anchor 12. It is preferred that left atrial anchor 12 have sufficient tension applied that the septum primum (SP) is brought into sealing apposition with the septum secundum (SS). This apposition, in many cases, may be enough to effectively close and seal the PFO. It may be preferable to also include a fabric or other covering with light atrial anchor 14 to help provide a seal to the PFO, as described above. If desired, at this point in the delivery method, the effectiveness of the closure and seal can again be tested by conventional techniques, such as those described above. If the seal is ineffective, closure device 10 can be removed as described later, and exchanged for a different device, for example, a device including a covering on arms 50 of right atrial anchor 14. Alternatively, the device 10 can be repositioned as described below.

Figure 10:
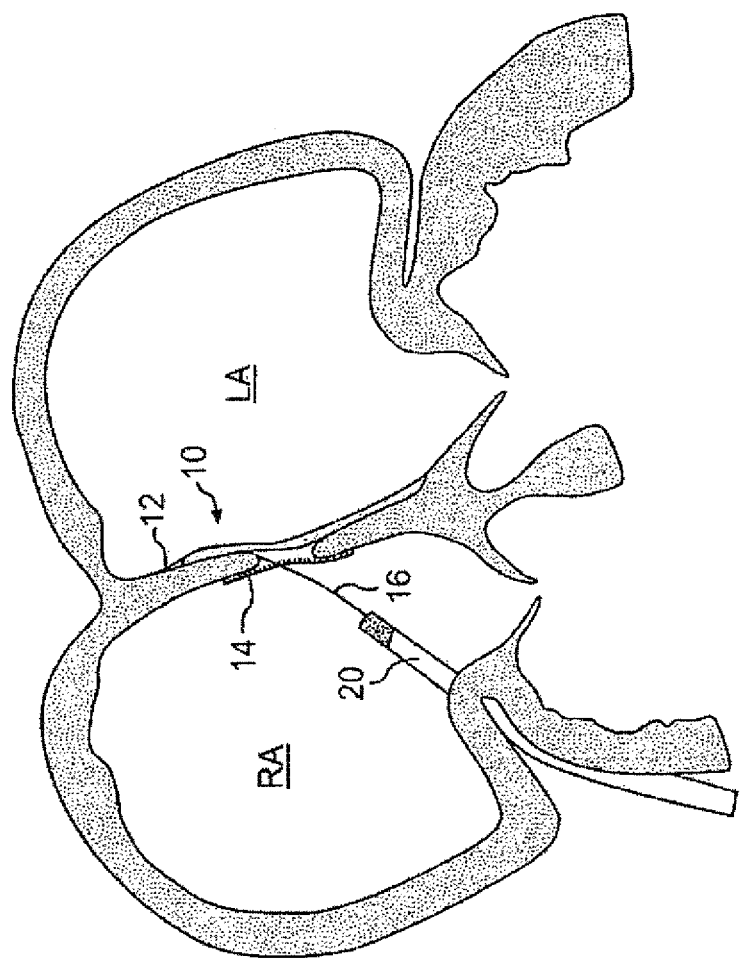
FIG. 10 is the right atrial anchor fixed to a tether of the closure device of FIG. 1, according to an embodiment of the present invention.

In the next step of an embodiment of the delivery method, right atrial anchor 14 is fixed to tether 16. FIGS. 12 and 13 show right atrial anchor 14 before it is fixed to tether 16. FIGS. 10 and 11 show right atrial anchor 14 after it is fixed to tether 16. As shown in the Figures, RPC 22 has been disengaged from right atrial anchor 14, which engages with a fixation mechanism 30 between right atrial anchor 14 and tether 16. Embodiments of such fixation mechanisms and their related methods to fix anchor 14 to tether 16 were described above. These devices and methods may provide a releasable fixation mechanism that is associated with RPC 22 so that the fixing of anchor 14 to tether 16 can be reversed at any time prior to severing of tether 16.

At this point, closure device 10 is in its final position, with the exception that flexible tether 16 extends between closure device 10 and guide catheter 20. Closure device 10, however, is essentially uninfluenced by guide catheter 20 or the extension of tether 16 to and through guide catheter 20. The effectiveness of the closure and sealing of the PFO can be tested by conventional techniques, such as contrast visualization, or a Valsalva maneuver combined with injection of bubbles, visualized with (TEE) or intracardiac ultrasound.

Additionally, at this stage of delivery of closure device 10, hemodynamic parameters such as oxygen saturation and pulmonary wedge pressure can be measured. In some rare instances, closure of a PFO may excessively increase pulmonary arterial pressure, in which case the closure device 10 can be removed, as described below. It may be necessary to leave the closure device in place for several hours or even days to fully assess the impact on hemodynamic parameters. If this is desired, the excess tether is simply left to extend from the closure device to the introduction site. At such time that the device is desired for permanent implantation, the excess tether is cut, or if the device is desired for removal, it is removed as described below.

Figure 17:
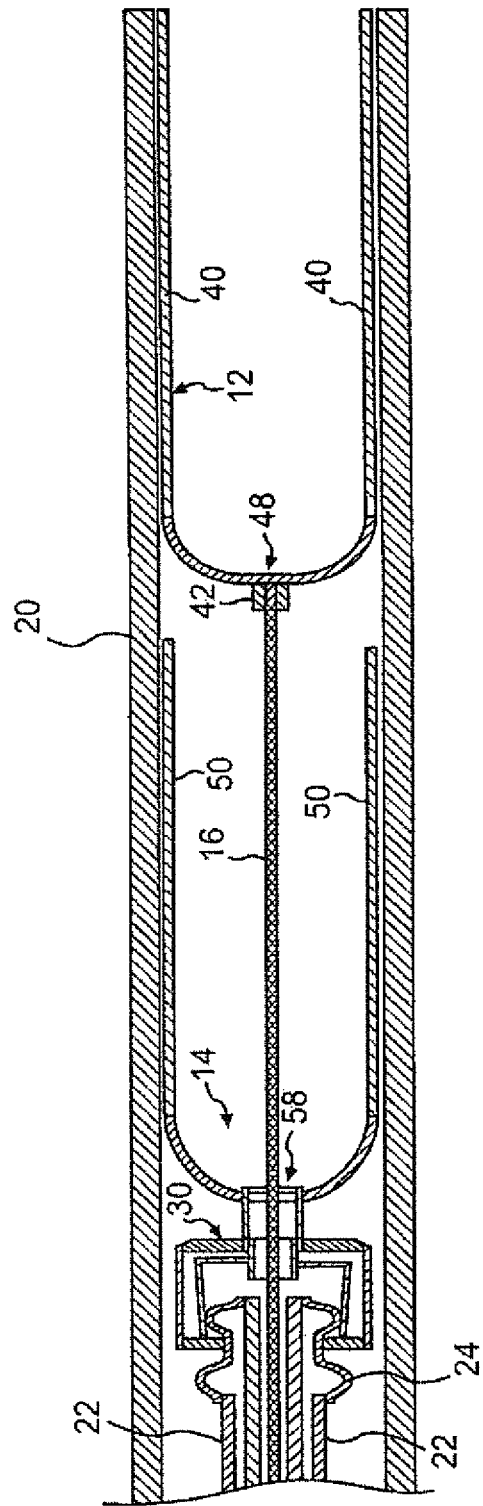
FIG. 17 is a cross sectional side view of the closure device, the positioning catheter, and the guide or delivery catheter of FIG. 15, with the closure device in a recaptured position within the guide catheter, according to an embodiment of the present invention.

At this point in the delivery method, or at any other earlier point in the procedure, closure device 10 can be completely removed from the patient. This may be necessary if, for example, device 10 is not creating a complete seal due to any of a number of causes, including, for example, the selected device being too small. To remove closure device 10, RPC 22 is re-engaged with right atrial anchor 14 to reverse the fixation mechanism that secures right atrial anchor 14 to tether 16. This allows right atrial anchor 14 to slide relative to tether 16. Right atrial anchor 14 may then be collapsed by retracting RPC 22 and right atrial anchor 14 within the delivery assembly 18, and specifically into guide catheter 20. Guide catheter 20 then may be re-advanced through the PFO track, while at the same time tension is maintained on tether 16. Continued advancement of guide catheter 20 will advance catheter 20 over left atrial anchor 12 to collapse anchor 12 within catheter 20 as shown in FIG. 17. The entire delivery assembly, including catheter 20, RPC 22, and collapsed closure device 10, may then be removed from the patient. In the alternative, closure device 10 may be redeployed and repositioned by repeating the delivery steps shown and described in connection with FIGS. 2 through 10 to obtain an effective seal of the PFO track.

If closure device 10, as shown in FIG. 10, results in satisfactory closure and sealing of the PFO, tether 16 is severed proximate right atrial anchor 14. This may be facilitated by removal of RPC 22 from guide catheter 20 and off of tether 16. A cutting device, such as, for example, a heated snare loop (not shown) or other suitable cutting device known in the art, may be positioned proximate right atrial anchor 14 to sever tether 16. This results in closure device 10 deployed as shown in FIG. 1.

Figure 21:
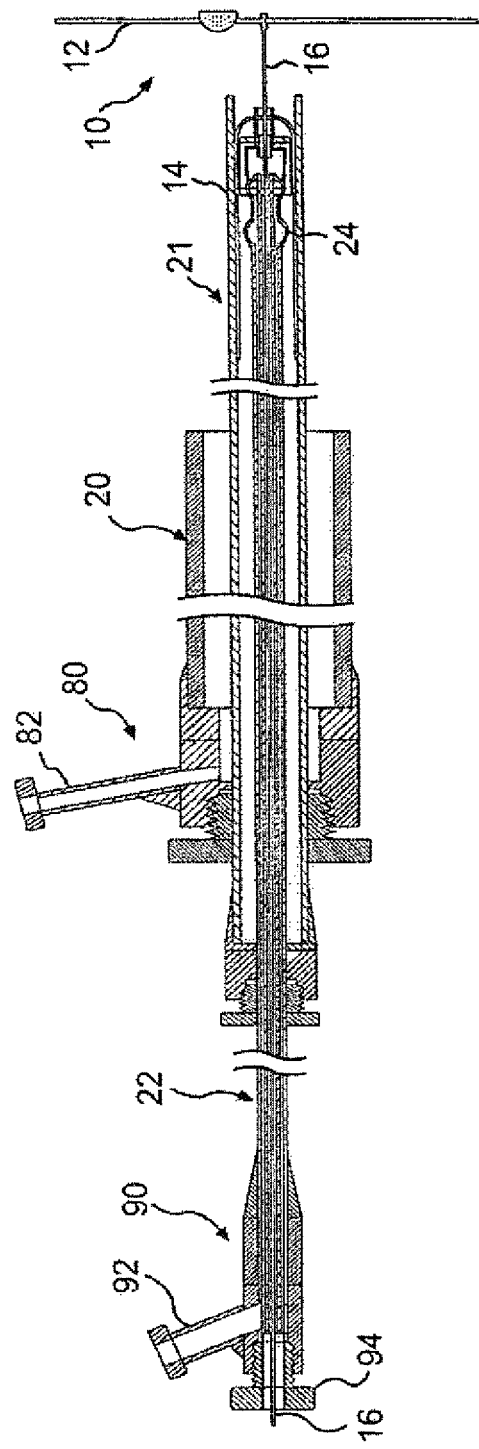
FIG. 21 is a longitudinal cross-section of a delivery system including a delivery sheath containing a closure device according to the present invention.

FIG. 21 illustrates an alternative embodiment for a delivery apparatus. In this embodiment, rather than positioning closure device 10 directly inside guide catheter 20, closure device 10 is prepackaged inside a delivery sheath 21. This entire assembly is then introduced into a conventional guide catheter 20. The delivery sheath 21 of this embodiment essentially serves the restraining functions of guide catheter 20 of the embodiment described in connection with FIG. 14. However, the embodiment of FIG. 21 does not require the separate step of loading closure device 10 just prior to introduction into the patient:

As mentioned above, closure device 10, according to one aspect of the invention, can be re-captured at any time prior and up to the state of closure device 10 depicted in FIG. 10. This permits repositioning of closure device 10 should, for example, device 10 not provide sufficient closure and sealing of the PFO. To recapture closure device 10, right atrial positioning catheter 22 is advanced along tether 16 and re-engaged with right atrial anchor 14. This reengagement occurs by positioning balloon 24 of RPC 22 within releasable fixation mechanism 30 and inflating balloon 24 to press balloon 24 against spring portions 32a, forcing piercing pins 32 out of and away from tether 16. Right atrial anchor 14 is then repositioned in guide catheter 20 so that arms 50 extend in a distal direction. This is done by pulling RPC 22 and right atrial anchor 14 into guide catheter 20, collapsing right atrial anchor 14 in a distal direction. Preferably, right atrial anchor 14 is positioned proximally enough within guide catheter 20 to leave space for left atrial anchor 12 within guide catheter 20. Guide catheter 20 is then advanced towards left atrial anchor 12 to collapse left atrial anchor 12 so that arms 40 also face distally. Alternatively, guide catheter 20 is held stationary and left atrial anchor 12 is retracted into guide catheter 20. The fully recaptured closure device is illustrated in FIG. 17.

Figure 18:
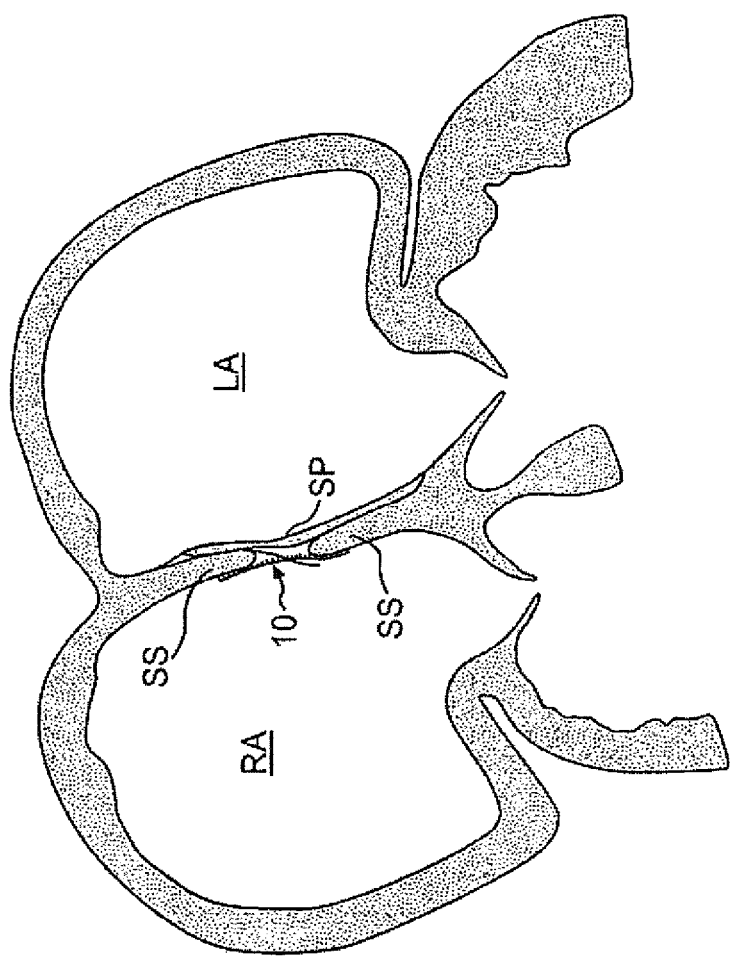
FIG. 18 is the closure device of FIG. 1 in a position covering a PFO where there is relatively short overlap between the septum primum and the septum secundum, according to an embodiment of the present invention.

The various described embodiments of closure devices and methods and tools for their delivery are suitable for closure of a wide variety of PFOs. For example, PFOs with a relatively long overlap between the septum primum (SP) and septum secundum (SS) may be suitably closed, as shown in FIG. 1. Also, PFOs with a relatively short overlap between the septum primum and septum secundum may be suitably dosed, as shown in FIG. 18.

Figure 19:
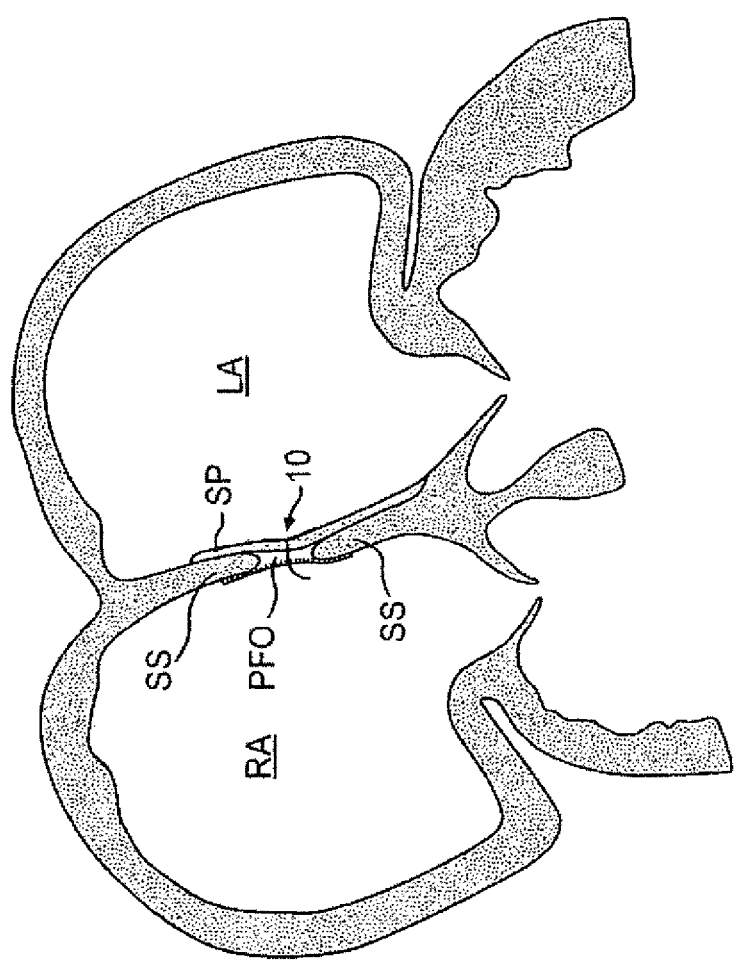
FIG. 19 is the closure device of FIG. 1 in a position covering a PFO after an access channel has been made into the left atrium, according to an embodiment of the present invention.
Figure 20:
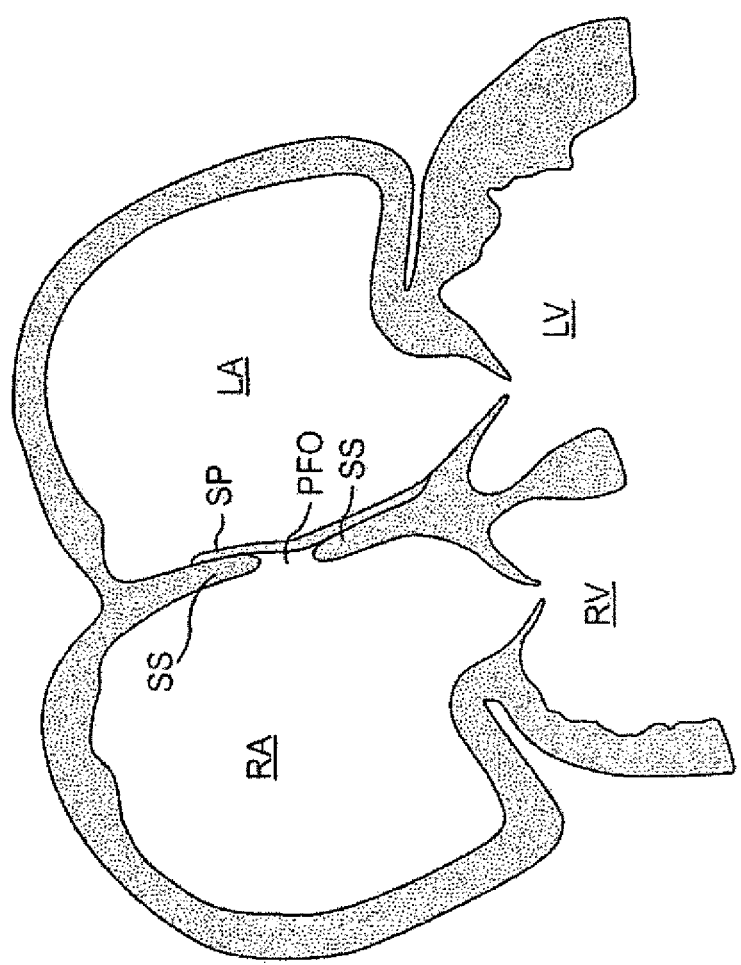
FIG. 20 is a longitudinal section of a portion of a heart having a PFO.

FIG. 19 illustrates an alternative method of delivery and use of closure device 10. In certain circumstances, the PFO track may not be ideally suited for delivery as described above. For example, the PFO track may be unusually long or unusually tight or may comprise more than one passage. A variety of electrophysiological procedures, such as left atrial mapping and/or ablations utilize an access channel into the left atrium by puncturing a small hole in the wall of the atrial septum primum. A similar technique can be utilized for positioning a guide catheter 20 through the septum primum. By utilizing these techniques, once a small hole is created in the septal wall, similar procedures as described above can be followed, resulting in closure device 10 positioned as shown in FIG. 19. Although closure device 10 does not sit entirely within the PFO track, a fabric covering on one or both of anchors 12 or 14 will effectively close the PFO.

Other embodiments of the invention will be apparent to those skilled in the art from consideration of the specification and practice of the invention disclosed herein. The specification and examples are exemplary, with a true scope and spirit of the invention being indicated by the following claims.

What is claimed is:

1. A device for sealing a passageway in a human heart, the device comprising:
   a first anchor adapted to be placed proximate a first end of the passageway, the first anchor deployable from a collapsed state to an expanded state, the first anchor having an open structure that permits blood to pass through the first anchor when the first anchor is in the expanded state;
   a second anchor adapted to be placed proximate a second end of the passageway, the second anchor deployable from a collapsed state to an expanded state, the second anchor having a covering for occluding blood flow through the second anchor when the second anchor is in the expanded state;
   an elongate member adapted to extend through the passageway and connect the first and second anchors; and
   a locking element positionable on the elongate member;
   wherein the second anchor is movable along the elongate member relative to the first anchor, wherein the locking element is movable along the elongate member towards the second anchor to secure the location of the second anchor on the elongate member, and wherein the locking element is arranged to engage the outer surface of the elongate member so as to permit movement of the locking element along the elongate member towards the second anchor but resist movement of the locking element along the elongate member away from the second anchor, whereby the locking element is configured to resist movement of the second anchor away from the first anchor along the elongate member.

2. The device of claim 1, wherein the passageway is a patent foramen ovale.

3. The device of claim 1, wherein the first anchor includes a plurality of arms radiating from a central hub of the first anchor.

4. The device of claim 1, wherein the second anchor includes a plurality of arms radiating from a central hub of the second anchor.

5. The device of claim 1, wherein the elongate member is flexible.

6. The device of claim 1, wherein the first anchor pivots relative to the elongate member.

7. The device of claim 1, wherein the second anchor pivots relative to the elongate member.

8. The device of claim 1, wherein the elongate member is capable of moving through the second anchor to vary a length of the elongate member between the first and second anchors.

9. The device of claim 1, wherein the elongate member is configured to move through the second anchor to vary a tension of the elongate member.

10. The device of claim 1, wherein the second anchor includes a plurality of arms, and wherein the covering spans between its plurality of arms.

11. The device of claim 10, wherein the first anchor includes a plurality of arms, and wherein the first anchor does not include structure spanning between its plurality of arms.

12. The device of claim 5, wherein the elongate member is sufficiently flexible to conform to a shape of the passageway.

13. The device of claim 1, wherein the elongate member is a braided structure.

14. The device of claim 1, wherein the elongate member is a multifilar structure.

15. The device of claim 1, wherein the elongate member is configured to permanently connect the first and second anchors implanted in the heart.

16. The device of claim 1, wherein at least a portion of the elongate member is configured to remain implanted in the heart with the device.

17. The device of claim 1, wherein the elongate member has a first end fixedly connected to the first anchor.

18. The device of claim 1, wherein the locking element is tubular.

19. A method of sealing a passageway in a heart, comprising:
   deploying a first anchor from a collapsed state to an expanded state, the first anchor having an open structure that permits blood to pass through the first anchor when the first anchor is in the expanded state;
   positioning the first anchor in the expanded state against a first portion of body tissue proximate a first end of the passageway;
   deploying a second anchor from a collapsed state to an expanded state, the second anchor having a covering for occluding blood flow through the second anchor when the second anchor is in the expanded state, the second anchor being movable along an elongate member relative to the first anchor, the elongate member extending through the passageway and connecting the first and second anchors;
   positioning the second anchor in the expanded state against a second portion of body tissue proximate a second end of the passageway; and
   moving a locking element along the elongate member towards the second anchor to secure the location of the second anchor on the elongate member, the locking element being arranged to engage the outer surface of the elongate member so as to permit movement of the locking element along the elongate member towards the second anchor but resist movement of the locking element along the elongate member away from the second anchor, whereby the locking element is configured to resist movement of the second anchor away from the first anchor along the elongate member.

20. The method of claim 19, wherein the passageway is a patent foramen ovale.

21. The method of claim 19, wherein moving the locking element along the elongate member towards the second anchor comprises moving the locking element to a position proximate the second anchor, whereby the locking element resists movement of the second anchor away from the first anchor.

22. The method of claim 21, further comprising severing the elongate member adjacent the second anchor.

23. The method of claim 19, wherein the second anchor includes a plurality of arms, and wherein the covering spans between its plurality of arms.

24. The method of claim 23, wherein the first anchor includes a plurality of arms, and wherein the first anchor does not include structure spanning between its plurality of arms.

25. The method of claim 20, wherein the elongate member is sufficiently flexible to conform to a shape of the patent foramen ovale.

26. The method of claim 19, further comprising moving the second anchor along the elongate member towards the first anchor prior to moving the locking element along the elongate member towards the second anchor.

27. The device of claim 1, wherein the locking element is movable along the elongate member to a position engaging the second anchor, whereby the locking element resists movement of the second anchor away from the first anchor.

28. The method of claim 19, wherein moving the locking element along the elongate member towards the second anchor comprises moving the locking element to a position engaging the second anchor, whereby the locking element resists movement of the second anchor away from the first anchor.

29. The device of claim 1, wherein the elongate member has a substantially smooth outer surface, and wherein the locking element includes a plurality of projecting grips arranged to engage the outer surface of the elongate member so as to permit movement of the locking element along the elongate member towards the second anchor but resist movement of the locking element along the elongate member away from the second anchor.

30. The method of claim 19, wherein the elongate member has a substantially smooth outer surface, and wherein the locking element includes a plurality of projecting grips arranged to engage the outer surface the outer surface of the elongate member so as to permit movement of the locking element along the elongate member towards the second anchor but resist movement of the locking element along the elongate member away from the second anchor.

31. The device of claim 1, wherein the covering of the second anchor comprises a porous material having a porosity sufficient to encourage ingrowth of tissue.

32. The device of claim 19, wherein the covering of the second anchor comprises a porous material having a porosity sufficient to encourage ingrowth of tissue.

* * * * *